US009018407B2

(12) United States Patent
Buck et al.

(10) Patent No.: US 9,018,407 B2
(45) Date of Patent: Apr. 28, 2015

(54) STEREOSELECTIVE SYNTHESIS OF BRIDGED METALLOCENE COMPLEXES

(71) Applicant: Chevron Phillips Chemical Company LP, The Woodlands, TX (US)

(72) Inventors: Richard M. Buck, Bartlesville, OK (US); Qing Yang, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 14/107,072

(22) Filed: Dec. 16, 2013

(65) Prior Publication Data
US 2014/0107363 A1 Apr. 17, 2014

Related U.S. Application Data

(63) Continuation of application No. 12/899,735, filed on Oct. 7, 2010, now Pat. No. 8,629,292.

(51) Int. Cl.
C07F 17/00 (2006.01)
C07F 19/00 (2006.01)

(52) U.S. Cl.
CPC ............... *C07F 19/00* (2013.01); *C07F 17/00* (2013.01)

(58) Field of Classification Search
None
See application file for complete search history.

(56) References Cited

U.S. PATENT DOCUMENTS

| | | |
|---|---|---|
| 3,242,099 A | 3/1966 | Manyik et al. |
| 3,248,179 A | 4/1966 | Norwood |
| 4,060,480 A | 11/1977 | Reed et al. |
| 4,452,910 A | 6/1984 | Hopkins et al. |
| 4,501,885 A | 2/1985 | Sherk et al. |
| 4,588,790 A | 5/1986 | Jenkins, III et al. |
| 4,794,096 A | 12/1988 | Ewen |
| 4,808,561 A | 2/1989 | Welborn, Jr. |
| 5,252,677 A | 10/1993 | Tomita et al. |
| 5,346,925 A | 9/1994 | Sugano et al. |
| 5,352,749 A | 10/1994 | Dechellis et al. |
| 5,376,611 A | 12/1994 | Shveima |
| 5,436,304 A | 7/1995 | Griffin et al. |
| 5,441,920 A | 8/1995 | Welborn, Jr. |
| 5,444,125 A | 8/1995 | Tomita et al. |
| 5,455,314 A | 10/1995 | Burns et al. |
| 5,468,781 A | 11/1995 | Sugano et al. |
| 5,565,175 A | 10/1996 | Hottovy et al. |
| 5,575,979 A | 11/1996 | Hason |
| 5,576,259 A | 11/1996 | Hasegawa et al. |
| 5,597,935 A | 1/1997 | Jordan et al. |
| 5,623,022 A | 4/1997 | Sugano et al. |
| 5,739,220 A | 4/1998 | Shamshoum et al. |
| 5,753,578 A | 5/1998 | Santi et al. |
| 5,807,938 A | 9/1998 | Kaneko et al. |
| 5,919,983 A | 7/1999 | Rosen |
| 5,948,873 A | 9/1999 | Santi et al. |
| 5,998,643 A | 12/1999 | Jordan et al. |
| 6,010,974 A | 1/2000 | Kim et al. |
| 6,107,230 A | 8/2000 | McDaniel et al. |
| 6,133,490 A | 10/2000 | Toyoda et al. |
| 6,153,777 A | 11/2000 | Jordan et al. |
| 6,165,929 A | 12/2000 | McDaniel et al. |
| 6,194,114 B1 | 2/2001 | Toyoda et al. |
| 6,207,608 B1 | 3/2001 | Jordan et al. |
| 6,218,469 B1 | 4/2001 | Morizono et al. |
| 6,239,235 B1 | 5/2001 | Hottovy et al. |
| 6,255,246 B1 | 7/2001 | Devore et al. |
| 6,262,191 B1 | 7/2001 | Hottovy et al. |
| 6,294,494 B1 | 9/2001 | McDaniel et al. |
| 6,300,271 B1 | 10/2001 | McDaniel et al. |
| 6,303,727 B1 | 10/2001 | Maeda et al. |
| 6,310,164 B1 | 10/2001 | Morizono et al. |
| 6,313,184 B1 | 11/2001 | Sasaki et al. |
| 6,316,553 B1 | 11/2001 | McDaniel et al. |
| 6,344,577 B1 | 2/2002 | Ewen |
| 6,355,594 B1 | 3/2002 | McDaniel et al. |
| 6,376,415 B1 | 4/2002 | McDaniel et al. |
| 6,388,017 B1 | 5/2002 | McDaniel et al. |
| 6,391,816 B1 | 5/2002 | McDaniel et al. |
| 6,395,666 B1 | 5/2002 | McDaniel et al. |
| 6,451,419 B1 | 9/2002 | Tsurugai et al. |
| 6,524,987 B1 | 2/2003 | Collins et al. |
| 6,531,552 B2 | 3/2003 | Nakano et al. |
| 6,548,441 B1 | 4/2003 | McDaniel et al. |
| 6,548,442 B1 | 4/2003 | Collins et al. |
| 6,562,918 B1 | 5/2003 | Minami et al. |
| 6,562,921 B1 | 5/2003 | Wenzel et al. |
| 6,576,583 B1 | 6/2003 | McDaniel et al. |
| 6,579,935 B1 | 6/2003 | Tanaka et al. |

(Continued)

FOREIGN PATENT DOCUMENTS

| | | |
|---|---|---|
| CN | 1276386 A | 12/2000 |
| CN | 1289784 A | 4/2001 |

(Continued)

OTHER PUBLICATIONS

Arnett et al., "Zero-Shear Viscosity of Some Ethyl Branched Paraffinic Model Polymers," Journal of Physical Chemistry, 1980, 84(6), pp. 649-652.

Biagini et al., "Synthesis and crystal structure of an ansa-disilylene-bridged zirconocene complex," Journal of Chemical Crystallography, 2001, 30(11), pp. 699-703.

Bird et al., "Dynamics of Polymeric Liquids," vol. 1, Fluid Mechanics, 2nd Edition, John Wiley & Sons, 1987, 3 pages.

Brenner et al., "Mixed Chloro(dialkylamido) Complexes of Zirconium and Hafnium," Z. anorg. Allg. Chem., 1995, 621, pp. 2021-2024.

(Continued)

*Primary Examiner* — Sudhakar Katakam
(74) *Attorney, Agent, or Firm* — Merchant & Gould

(57) ABSTRACT

The present invention provides methods of making stereo-enriched ansa-metallocene compounds using an unchelated amine compound. Generally, these methods result in a rac: meso isomer selectivity of the stereo-enriched ansa-metallocene compound of greater than 4:1.

22 Claims, 1 Drawing Sheet

(56) References Cited

U.S. PATENT DOCUMENTS

| | | |
|---|---|---|
| 6,613,712 B1 | 9/2003 | McDaniel et al. |
| 6,620,894 B2 | 9/2003 | Sachs |
| 6,632,885 B2 | 10/2003 | Morizono et al. |
| 6,632,894 B1 | 10/2003 | McDaniel et al. |
| 6,667,274 B1 | 12/2003 | Hawley et al. |
| 6,750,302 B1 | 6/2004 | McDaniel et al. |
| 6,825,280 B1 | 11/2004 | Hayakawa et al. |
| 6,833,045 B1 | 12/2004 | Tokita et al. |
| 6,833,415 B2 | 12/2004 | Kendrick et al. |
| 6,887,943 B2 | 5/2005 | Onoe et al. |
| 6,891,018 B2 | 5/2005 | Murakami et al. |
| 6,897,273 B2 | 5/2005 | Szul et al. |
| 7,019,080 B2 | 3/2006 | Kashihara et al. |
| 7,026,494 B1 | 4/2006 | Yang et al. |
| 7,041,617 B2 | 5/2006 | Jensen et al. |
| 7,064,225 B2 | 6/2006 | Thorn et al. |
| 7,115,694 B2 | 10/2006 | Shimizu et al. |
| 7,119,153 B2 | 10/2006 | Jensen et al. |
| 7,122,604 B2 | 10/2006 | Onoe et al. |
| 7,148,298 B2 | 12/2006 | Jensen et al. |
| 7,199,073 B2 | 4/2007 | Martin et al. |
| 7,226,886 B2 | 6/2007 | Jayaratne et al. |
| 7,259,215 B2 | 8/2007 | Kanamaru et al. |
| 7,294,599 B2 | 11/2007 | Jensen et al. |
| 7,312,283 B2 | 12/2007 | Martin et al. |
| 7,420,097 B2 | 9/2008 | Thorn et al. |
| 7,468,452 B1 | 12/2008 | Martin et al. |
| 7,517,939 B2 | 4/2009 | Yang et al. |
| 7,521,572 B2 | 4/2009 | Jayaratne et al. |
| 7,572,948 B2 | 8/2009 | Martin et al. |
| 7,619,047 B2 | 11/2009 | Yang et al. |
| 7,863,210 B2 | 1/2011 | Murray et al. |
| 7,884,163 B2 | 2/2011 | McDaniel et al. |
| 7,919,639 B2 | 4/2011 | Murray et al. |
| 8,012,900 B2 | 9/2011 | Murray et al. |
| 8,080,681 B2 | 12/2011 | Murray et al. |
| 8,114,946 B2 | 2/2012 | Yang et al. |
| 8,228,487 B2 | 7/2012 | Rijpma et al. |
| 8,609,793 B2 | 12/2013 | Buck et al. |
| 8,629,292 B2 | 1/2014 | Buck et al. |
| 8,637,616 B2 | 1/2014 | Buck et al. |
| 2002/0119890 A1 | 8/2002 | Wenzel |
| 2003/0134991 A1 | 7/2003 | Tanaka et al. |
| 2004/0059070 A1 | 3/2004 | Whitte |
| 2004/0132917 A1 | 7/2004 | Masi et al. |
| 2005/0159300 A1 | 7/2005 | Jensen et al. |
| 2009/0137755 A1 | 5/2009 | Yamada et al. |
| 2010/0076167 A1 | 3/2010 | McDaniel et al. |
| 2010/0292425 A1 | 11/2010 | Yang et al. |
| 2010/0317904 A1 | 12/2010 | Small |
| 2010/0331505 A1 | 12/2010 | Masino et al. |
| 2011/0082323 A1 | 4/2011 | Small et al. |
| 2011/0257348 A1 | 10/2011 | Yang et al. |
| 2012/0010375 A1 | 1/2012 | Yang et al. |
| 2012/0088890 A1 | 4/2012 | Buck et al. |
| 2012/0088924 A1 | 4/2012 | Buck et al. |
| 2012/0232229 A1 | 9/2012 | Buck et al. |
| 2014/0057777 A1 | 1/2014 | Buck et al. |
| 2014/0107301 A1 | 4/2014 | Buck et al. |

FOREIGN PATENT DOCUMENTS

| | | |
|---|---|---|
| CN | 1176113 C | 11/2004 |
| DE | 19847320 | 4/2000 |
| EP | 0 752 428 | 1/1997 |
| EP | 0 692 505 | 11/1997 |
| EP | 0 806 436 | 11/1997 |
| EP | 0 849 273 | 6/1998 |
| EP | 2 177 543 | 4/2010 |
| JP | 2002047295 | 2/2002 |
| JP | 2002308893 | 10/2002 |
| JP | 2004175707 | 6/2004 |
| JP | 2004367687 | 11/2009 |
| WO | WO 0246250 A2 | 6/2002 |
| WO | WO 0250127 A2 | 6/2002 |

OTHER PUBLICATIONS

Buck et al., "Control of ansa-Zirconocene Stereochemistry by Reversible Exchange of Cyclopentadienyl and Chloride Ligands," J. Am. Chem. Soc., 2007, 129, pp. 3468-3469.

Christopher et al., "Synthesis and Structures of rac-Me$_2$Si($\eta^5$-1-indenyl)$_2$Hf(NMe$_2$)$_2$ and {Me$_2$Si($\eta^5$-1-indenyl)($\eta^3$-2-indenyl)}Hf(NMe$_2$)$_2$," Organometallics, 1997, 16, pp. 3044-3050.

Christopher et al., "Synthesis, Structure, and Reactivity of rac-Me$_2$Si(indenyl)$_2$Zr(NMe$_2$)$_2$," Organometallics, 1996, 15, pp. 4038-4044.

Cotton et al., Advanced Inorganic Chemistry, 6th Ed., Wiley-Interscience, 1999, 4 pages.

DesLauriers et al., "Quantifying short chain branching microstructures in ethylene 1-olefin copolymers using size exclusion chromatography and Fourier transform infrared spectroscopy (SEC-FTIR)," Polymer, 2002, 43, pp. 159-170.

Diamond et al., "Efficient Synthesis of chiral ansa-Metallocenes by Amine Elimination. Synthesis, Structure, and Reactivity of rac-(EBI)Zr(NMe$_2$)$_2$," J. Am. Chem. Soc., 1996, 118, pp. 8024-8033.

Diamond et al., "Efficient Synthesis of rac-(Ethylenebis(indenyl))ZrX$_2$ Complexes via Amine Elimination," Organometallics, 1995, 14, pp. 5-7.

Diamond et al., "Synthesis of Group 4 Metal rac-(EBI)M(NR$_2$)$_2$ Complexes by Amine Elimination. Scope and Limitations," Organometallics, 1996, 15, pp. 4030-4037.

Diamond et al., "Synthesis of Me$_2$Si-Bridged ansa-Zirconocenes by Amine Elimination," Organometallics, 1996, 15, pp. 4045-4053.

Dunn et al., "Computational Modeling of ansa-Zirconocene Amide Complexes," Organometallics, 2004, 23, pp. 5671-5680.

Hawley's Condensed Chemical Dictionary, 11th Ed., John Wiley & Sons, 1995, 3 pages.

Hieber et al., "Shear-Rate-Dependence Modeling of Polymer Melt Viscosity," Polymer Engineering and Science, 1992, 32(14), pp. 931-938.

Hieber et al., "Some correlations involving the shear viscosity of polystyrene melts," Rheologica Acta, 1989, 28, pp. 321-332.

Janzen et al., "Diagnosing long-chain branching in polyethylenes," Journal of Molecular Structure, 1999, 485-486, pp. 569-584.

Jutzi et al., "$\pi$-H$_3$C$_5$(Me$_2$Si)(Me$_2$SiSiMe$_2$)-$\pi$-C$_5$H$_3$: a novel double-bridged dicyclopentadienyl ligand. Synthesis and application in complex chemistry," Journal of Organometallic Chemistry, 1997, 541(1-2), pp. 9-17.

Kim et al., "In situ activation of rac-(SBI)Zr(NMe$_2$)$_2$ for the polymerization of propylene," Polymer Bulletin (Springer-Verlag), 1997, 39, 2 pages.

Köppl et al., "Homopolymerization of ethylene and copolymerization of ethylene and 1-hexene with bridged metallocene/methylaluminoxane catalysts: the influence of the bridging moiety," Journal of Molecular Catalysis A: Chemical, 2000, 153(1-2), pp. 109-119.

Li et al., "Coordination Copolymerization of Severely Encumbered Isoalkenes with Ethylene: Enhanced Enchainment Mediated by Binuclear Catalysts and Cocatalysts," J. Am. Chem. Soc., 2005, 127, pp. 14756-14768.

LoCoco et al., "Chelate-Controlled Synthesis of rac-and meso-Me$_2$Si(3-$^t$Bu-C$_5$H$_3$)$_2$ZrCl$_2$," Organometallics, 2003, 22, pp. 5498-5503.

LoCoco et al., "Chelate-Controlled Synthesis of Racemic ansa-Zirconocenes," J. Am. Chem. Soc., 2004, 126, pp. 15231-15244.

LoCoco et al., "Enantioselective Synthesis of ansa-Zirconocenes," J. Am. Chem. Soc., 2004, 126, pp. 13918-13919.

Pérez-Camacho et al., "Si$_2$Me$_4$-bridged zirconocene dichlorides: crystal and molecular structure of meso-Si$_2$Me$_4$(3-SiMe$_3$-C$_9$H$_5$)$_2$ZrCl$_2$," Journal of Organometallic Chemistry, 1999, 585, pp. 18-25.

Pinnavaia, "Intercalated Clay Catalysts," Science, 1983, 220(4595), pp. 365-371.

(56) References Cited

OTHER PUBLICATIONS

Schertl et al., "ansa-Bis(fluorenyl) complexes of zirconium and hafnium with silicon in the bridge: synthesis and polymerization properties," Journal of Organometallic Chemistry, 1997, 545-546, pp. 553-557.

Thiele et al., "Tetramethyldisilane-1,2-diyl bridged dicyclopentadienyl and diindenyl metal dichlorides of the Group 4 metals—crystal structure of [cyclic] $C_5H_4\text{-SiMe}_2\text{-}C_5H_4ZrCl_2$," Z. anorg. Allg. Chem, 1996, 622(10), pp. 1806-1810.

Thiyagarajan et al., "Aluminum *ansa*-Indenyl Compounds. Synthesis, Structures, Dynamic Properties, and Application in the Synthesis of Group 4 *ansa*-Metallocenes," Organometallics, 1999, 18, pp. 5347-5359.

Thomas, "Sheet Silicate Intercalates: New Agents for Unusual Chemical Conversions*," Intercalation Chemistry (S. Whittington and A. Jacobson, eds.), Academic Press, Inc. Ch. 3, 1972, pp. 55-99.

Tian et al., "Crystal structures and polymerization catalytic properties of 1,1,2,2-tetramethyldisilane-bis(3-t-butyl-η 5-cyclopentadienyl) titanium and zirconium dichlorides," Journal of Organometallic Chemistry, 1999, 579(1-2), pp. 24-29.

Tian et al., "Ethylene polymerization with sila-bridged dinuclear zirconocene catalysts," Macromolecular Chemistry and Physics, 2002, 203(1), pp. 31-36.

Wigum et al., "Structure-property transition-state model for the copolymerization of ethene and 1-hexene with experimental and theoretical applications to novel disilylene-bridged zirconocenes," Polymer Chemistry, 2003, 41(11), pp. 1622-1631.

Wild et al., "*ansa*-Metallocene Derivatives: IV. Synthesis and molecular structures of chiral *ansa*-titanocene derivatives with bridged tetrahydroindenyl ligands,"Journal of Organometallic Chemistry, 1982, 232(3), 3 pages.

Wiley InterScience, Angewandte Chemie International Edition in English, http://www3.interscience.wiley.com/journal/106581873/abstract?CRETRY=1&SRETRY=0, 1979, 18, 2 pages.

Zachmanoglou et al., "Chiral *Ansa* Zirconocene Compounds with [MeSi] and [MeSi] Bridges and with *tert*-Butyl Ring Substituents: Synthesis and Structural Chracterization of the *Racemo* Complexes *rac*-[MeSi(Ch-2,4-Bu)]ZrC1 and *rac*-[MeSi(Ch-2,4-Bu)]ZrCl," Organometallics, 2005, 24(4), pp. 603-611.

Zachmanoglou et al., "The Electronic Influence of Ring Substituents and Ansa Bridges in Zirconocene Complexes as Probed by Infrared Spectroscopic, Electrochemical, and Computational Studies," Journal of the American Chemical Society, 2002, 124(32), pp. 9525-9546.

Zhang et al., "General Synthesis of Racemic $Me_2Si$-Bridged Bis(indenyl) Zirconocene Complexes," J. Am. Chem. Soc., 2000, 122, pp. 8093-8094.

Wang et al., "Ansa-metallocene Complexes (III)—Synthesis and Application in Ethylene Polymerization of Sila-bridged Bis(indenyl and tetrahydroindenyl) Titanium and Zirconium Complexes," Chemical Journal of Chinese Universities, vol. 20 (1), 1999, p. 80.

Wyatt, "Light scattering and the absolute characterization of macromolecules," Wyatt Technology Corporation, Analytica Chimica Acta, 272, 1993, pp. 1-40.

Xiu-Li et al., "ansa-Metallocene Complexes(IV)—Synthesis, Structure and Application in Ethylene Polymerization of Sila-bridged Substituted Cyclopentadienyl Titanium and Zirconium," Chemical Research in Chinese Universities, 2000, 4 pages.

Ying et al., "Synthesis and Structure of 1,1'—(Tetramethyldisilandiy1)η~5-Dicyclopentadienyl Zirconium Dibromide," Chemical Research in Chinese Universities, 1991, 1 page.

Tumay, TA, et al., "*Ring-Closing Metathesis of Sterically Congested Functionalized Zirconocenes-ethene Polymerization Catalysts Derived from Related Bridged and Open Metallocenes,* " Dalton Transactions, No. 41, 2009, pp. 8923-8928.

Wang, B., et al., "*Ansa-Metallocene Polymerization Catalysts: Effects of the Bridges on the Catalytic Activities*," Coordination Chemistry Reviews, vol. 250, No. 1-2, Jan. 2006, pp. 242-258.

Cho, YJ, et al., "*Molecular Structure of Rac-Cis-1,4-2-Butenylenebis(l-denyl)zirconium Dichloride, Bulletin of the Korean Chemical Society*", vol. 20, No. 3, Mar. 20, 1999, pp. 362-364.

Park, JT, et al., "*An Efficient Synthetic Method of Ansa-Zirconocene Dimethyl Complexes Via Me2ZrCI2,*" Journal of Organometallic Chemistry, vol. 5325, No. 1-2, May 15, 1997, pp. 29-32.

*Modern Plastics Encyclopedia*, Mid-Nov. 1995 Issue, vol. 72, No. 12, 3 pages.

*Film Extrusion Manual—Process, Materials, Properties*, TAPPI Press, 1992, 13 pages.

International Search Report for PCT/US2011/055070 dated Feb. 2, 2012. 6 pages.

Partial International Search Report for PCT/US2011/055026 dated Jun. 12, 2012. 3 pages.

International Search Report for PCT/US2013/034373 dated Aug. 20, 2013, 3 pages.

U.S. Office Action in U.S. Appl. No. 13/437,277 dated Mar. 28, 2013, 18 pages.

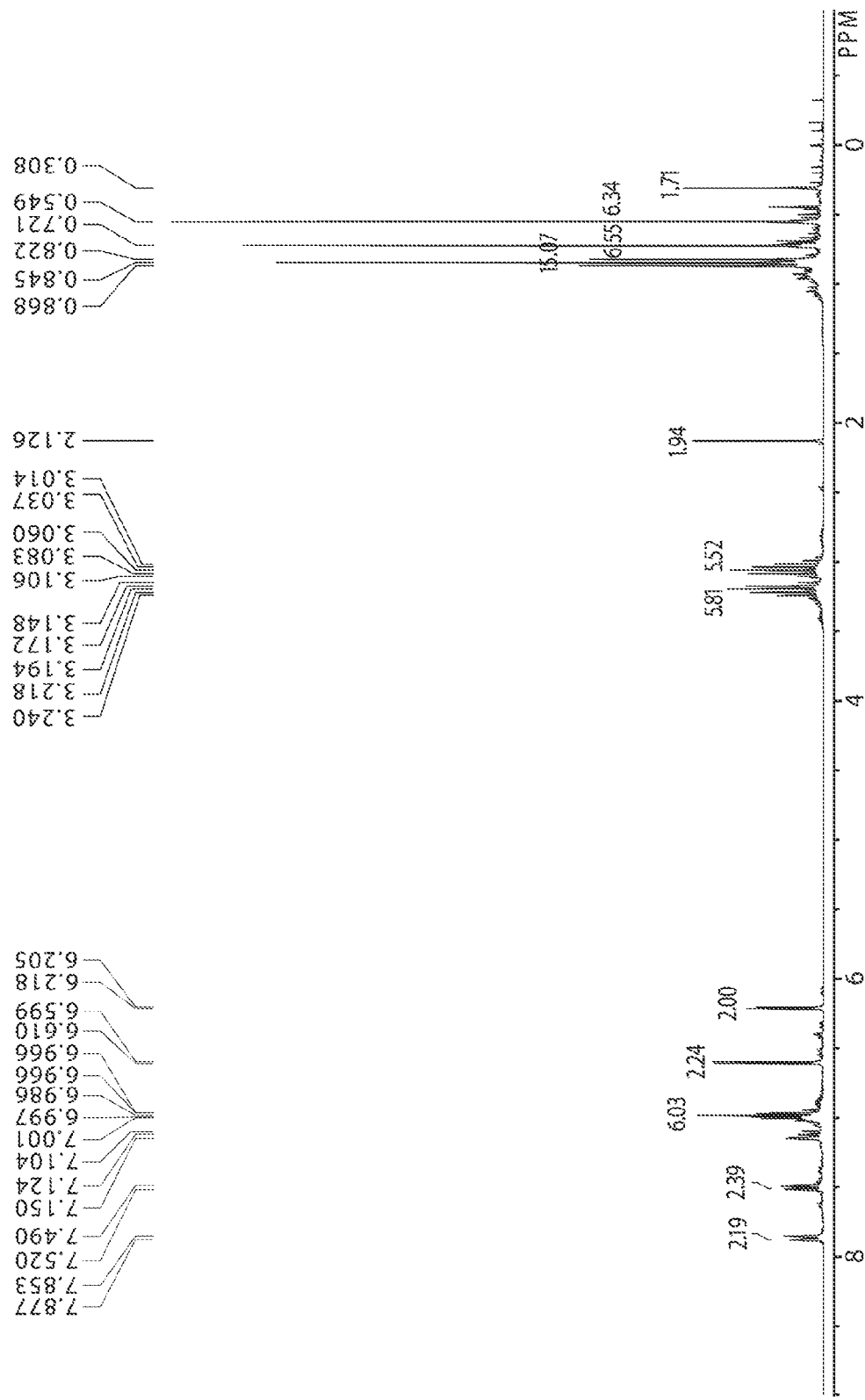

STEREOSELECTIVE SYNTHESIS OF BRIDGED METALLOCENE COMPLEXES

This application is a continuation application of co-pending U.S. patent application Ser. No. 12/899,735, filed on Oct. 7, 2010, now U.S. Pat. No. 8,629,292, the disclosure of which is incorporated herein by reference in its entirety.

BACKGROUND OF THE INVENTION

The present invention relates generally to the synthesis of ansa-metallocene compounds. These ansa-metallocene compounds may be used as components in a multi-component catalyst system, ultimately for use in olefin polymerizations or other catalytic processes. More specifically, this invention relates to methods for the stereoselective synthesis of certain bridged metallocene compounds.

Often, an isomer of a particular ansa-metallocene compound, such as the rac isomer instead of the meso isomer, may provide performance advantages such as improved control of tacticity, e.g., for producing isotactic polypropylene. However, isolating and purifying a desired isomer from a rac/meso isomer mixture may be very difficult, and is not always possible.

It would be beneficial to develop new synthetic methods to produce stereo-enriched ansa-metallocenes in an acceptable isomer selectivity such that additional isolation or purification steps are neither necessary nor required. Accordingly, it is to this end that the present invention is directed.

SUMMARY OF THE INVENTION

The present invention discloses methods for synthesizing ansa-metallocene compounds. These compounds can be used in catalyst systems for the polymerization of olefins and other catalytic processes where stereoselectivity may be important.

Methods of making stereo-enriched ansa-metallocene compounds having the formula:

$$E(CpR^A{}_n)_2M(NR_2)_m \qquad (I),$$

are disclosed.

In accordance with an aspect of this invention, a method of making a stereo-enriched ansa-metallocene compound having formula (I) uses a compound having formula (II) and an unchelated amine compound having formula (III) as starting materials. This method comprises:

reacting a compound having formula (II):

$$E(CpR^A{}_n)_2M^A{}_2 \qquad (II)$$

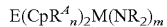

with an unchelated amine compound having formula (III):

$$M(NR_2)_m X_p L_q \qquad (III);$$

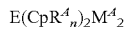

wherein:

M is Ti, Zr, Hf, Cr, Sc, Y, La, or a lanthanide;

Cp is a cyclopentadienyl, indenyl, or fluorenyl group;

E is a substituted or unsubstituted bridging chain of 3 to 8 carbon atoms or 2 to 8 silicon, germanium, or tin atoms, wherein any substituents on atoms of the bridging chain independently are H or a hydrocarbyl group having up to 18 carbon atoms;

each R independently is H, a hydrocarbyl, hydrocarbylsilyl, hydrocarbylamino, or hydrocarbyloxide group having up to 18 carbon atoms, or each $NR_2$ group is a heterocyclic group having up to 18 carbon atoms;

each $R^A$ independently is H or a hydrocarbyl, hydrocarbylsilyl, hydrocarbylamino, or hydrocarbyloxide group having up to 18 carbon atoms;

m is 2, p is 2, and q is 0, 1, or 2 when M is Ti, Zr, or Hf;

m is 1, p is 2, and q is 0, 1, 2, or 3 when M is Cr, Sc, Y, La, or a lanthanide;

n is 0, 1, 2, 3, or 4 when Cp is an indenyl group;

n is 1, 2, 3, or 4 when Cp is a cyclopentadienyl or a fluorenyl group;

each $M^A$ independently is Li, Na, K, $SiR^B{}_3$, $AlR^B{}_2$, $SnR^B{}_3$, ½ Mg, ½ Zn, MgX, or ZnX, wherein $R^B$ is an alkyl group having up to 18 carbon atoms;

each X independently is triflate, a halide, or a sulfonate; and each L independently is a neutral Lewis base donor ligand.

In another aspect of this invention, a method of making a stereo-enriched ansa-metallocene compound having formula (I) using a different starting material is disclosed. For instance, the stereo-enriched ansa-metallocene compound having formula (I) can be synthesized from a compound having formula (IV):

$$E(CpR^A)_2 \qquad (IV),$$

wherein E, Cp, $R^A$, and n are as defined above.

Generally, the synthesis methods disclosed herein can result directly in a stereo-enriched ansa-metallocene compound having a 4:1 or greater isomer ratio—e.g., a molar ratio of the rac isomer to the meso isomer of the ansa-metallocene compound having formula (I) of greater than about 5:1 or, alternatively, greater than about 10:1. Additionally, these synthesis methods do not require subsequent purification of the rac/meso isomer mixture in order to achieve the stereoselectivity of 4:1 or more in the rac isomer.

The present invention also is directed to rac-ansa-metallocene compounds having formula (I), and to compositions comprising an ansa-metallocene compound having formula (I) with a rac:meso isomer ratio of greater than 4:1.

BRIEF DESCRIPTION OF THE FIGURE

FIG. 1 presents a $^1$H-NMR plot of the final product of Example 4 containing rac-MET2.

DEFINITIONS

To define more clearly the terms used herein, the following definitions are provided. To the extent that any definition or usage provided by any document incorporated herein by reference conflicts with the definition or usage provided herein, the definition or usage provided herein controls.

The term "polymer" is used herein generically to include olefin homopolymers, copolymers, terpolymers, and so forth. A copolymer is derived from an olefin monomer and one olefin comonomer, while a terpolymer is derived from an olefin monomer and two olefin comonomers. Accordingly, "polymer" encompasses copolymers, terpolymers, etc., derived from any olefin monomer and comonomer(s) disclosed herein. Similarly, an ethylene polymer would include ethylene homopolymers, ethylene copolymers, ethylene terpolymers, and the like. As an example, an olefin copolymer, such as an ethylene copolymer, can be derived from ethylene and a comonomer, such as 1-butene, 1-hexene, or 1-octene. If the monomer and comonomer were ethylene and 1-hexene, respectively, the resulting polymer would be categorized an as ethylene/1-hexene copolymer.

In like manner, the scope of the term "polymerization" includes homopolymerization, copolymerization, terpolymerization, etc. Therefore, a copolymerization process would involve contacting one olefin monomer (e.g., ethylene) and one olefin comonomer (e.g., 1-hexene) to produce a copolymer.

The term "contact product" is used herein to describe compositions wherein the components are contacted together in any order, in any manner, and for any length of time. For example, the components can be contacted by blending or mixing. Further, contacting of any component can occur in the presence or absence of any other component. Combining additional materials or components can be done by any suitable method. Further, the term "contact product" includes mixtures, blends, solutions, slurries, reaction products, and the like, or combinations thereof. Although "contact product" can include reaction products, it is not required for the respective components to react with one another. Similarly, the term "contacting" is used herein to refer to materials which may be blended, mixed, slurried, dissolved, reacted, treated, or otherwise contacted in some other manner. Therefore, the term "contacting" encompasses the "reacting" of two or more components, and it also encompasses the "mixing" or "blending" of two or more components that do not react with one another.

The term "in the presence of" a particular solvent is used herein to indicate that the components that are contacted or reacted in steps of a synthesis can occur "in" the solvent (e.g., in solution), but this is not a requirement. For instance, one or more of the components can be dissolved in the solvent. Additionally or alternatively, one or more of the components can be partially or completely insoluble in the solvent. Thus, the use of "in the presence of" a particular solvent is meant to include both single phase and multi-phase reaction systems. In many cases, one component can be dissolved in a solvent when contacted or reacted with one or more other components.

The term "stereo-enriched," as used herein, denotes a compound having at least a 4:1 isomer ratio, i.e., either the rac:meso or meso:rac isomer ratio of the compound is greater than 4:1, depending upon whether the compound is rac-enriched or meso-enriched. For example, "stereo-enriched" can refer to a metallocene compound having a rac:meso stereoselectivity of greater than 4:1.

The term "metallocene," as used herein, describes a compound comprising at least one $\eta^3$ to $\eta^5$-cycloalkadienyl-type moiety, wherein $\eta^3$ to $\eta^5$-cycloalkadienyl moieties include cyclopentadienyl ligands, indenyl ligands, fluorenyl ligands, and the like, including partially saturated or substituted derivatives or analogs of any of these. Possible substituents on these ligands may include H, therefore this invention comprises partially saturated ligands such as tetrahydroindenyl, tetrahydrofluorenyl, octahydrofluorenyl, partially saturated indenyl, partially saturated fluorenyl, and the like.

A Cp group (cyclopentadienyl, indenyl, fluorenyl) exhibits two faces through which coordination to a metal may occur. The symmetry relations existing between these two faces determine the type of stereoisomers that can potentially form upon coordination. This facial symmetry is determined, in turn, by the number and type of $R^4$ substituents on the Cp. If the uncoordinated Cp contains a two-fold rotation axis, or equivalently, possesses a perpendicular mirror plane, the faces are homotopic (i.e., equivalent). The Cp is therefore termed "achiral" and its coordination to a metal results only in a single isomer. The $R^4$ substituents may or may not possess chirality of their own; the free rotation of $R^4$ substituents about their respective Cp-$R^4$ bonds is assumed in the definitions provided herein.

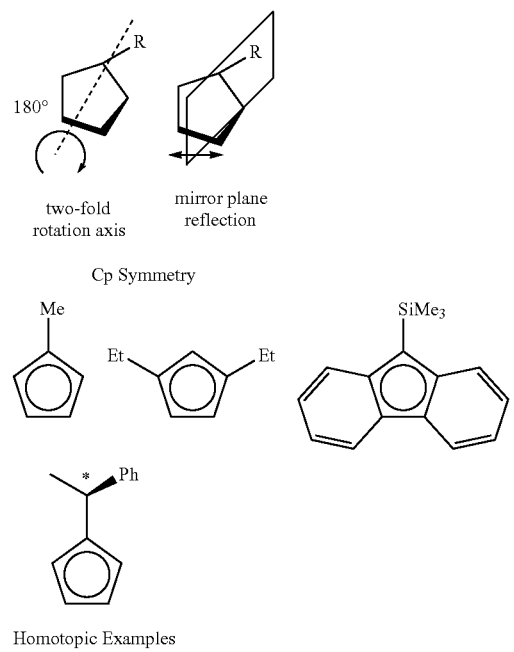

Cp Symmetry

Homotopic Examples

If the uncoordinated Cp does not contain a two-fold axis or perpendicular mirror plane, and the $R^4$ substituents do not possess chirality of their own, the faces are enantiotopic (i.e., mirror images of one another). The Cp is therefore termed "prochiral" and its coordination to metal results in two enantiomers. The overall chirality exhibited by the metal-Cp complex arises from coordination of the planar Cp and is termed planar chirality. Stereochemical descriptors R and S are assigned based on the Cahn-Ingold-Prelog nomenclature known to those of skill in the art.

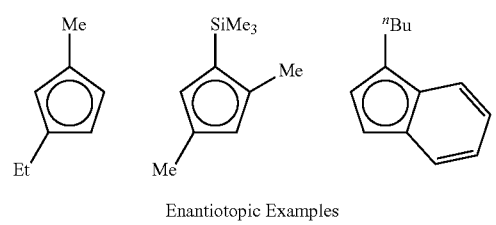

Enantiotopic Examples

If the uncoordinated Cp does not contain a two-fold axis or perpendicular mirror plane, and the $R^4$ substituents do possess chirality of their own, the faces are diastereotopic. The Cp is prochiral in this case as well, and its coordination to a metal results in two diastereomers (i.e., not mirror images of one another).

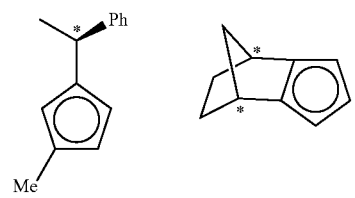

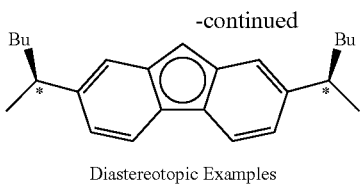

Diastereotopic Examples

In the case of two identical, achiral Cp groups linked by a bridge, in which the bridging atom or group itself is counted as a substituent for the purpose of designating the chirality of the Cp groups, coordination to a metal can result in only a single isomer.

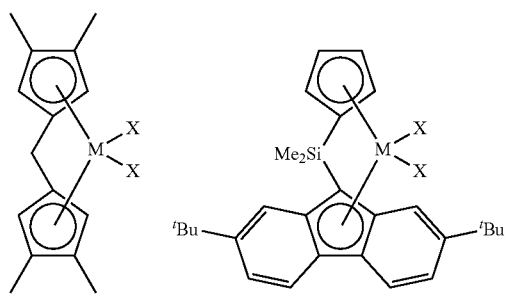

Bridged Achiral General Examples

In the case of two identical, prochiral Cp groups lacking $R^A$ chirality, linked by a bridge, in which the bridging atom or group itself is counted as a substituent for the purpose of designating the chirality of the Cp groups, the coordination to a metal can result in two possible diastereomers, one achiral (mesa) and one chiral (racemic or rac). The rac diastereomer is comprised of two enantiomers. In this disclosure, the methods, compounds, and compositions disclosed herein pertain only to ansa-metallocenes exhibiting prochiral Cp groups.

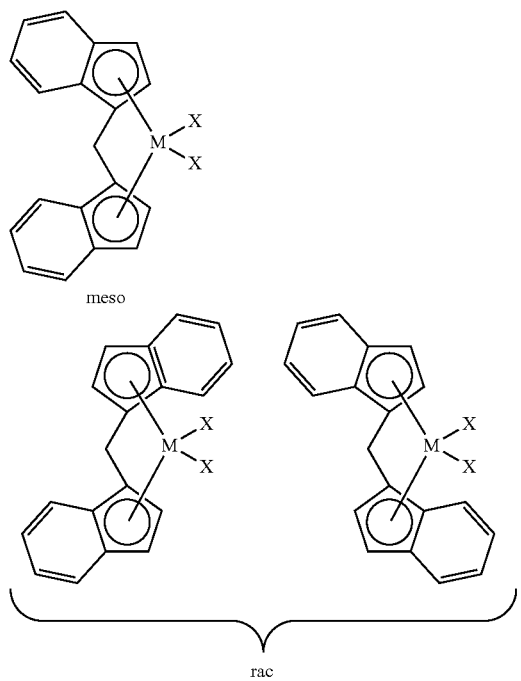

Bridged Prochiral General Example

For any particular compound disclosed herein, any general or specific structure presented also encompasses all conformational isomers, regioisomers, and stereoisomers that may arise from a particular set of substituents, unless stated otherwise. Also, unless stated otherwise, the general or specific structure also encompasses all enantiomers, diastereomers, and other optical isomers whether in enantiomeric or racemic forms, as well as mixtures of stereoisomers, as would be recognized by a skilled artisan.

Although any methods, devices, and materials similar or equivalent to those described herein can be used in the practice or testing of the invention, the typical methods, devices and materials are herein described.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

Applicants disclose several types of ranges in the present invention. These include, but are not limited to, a range of number of atoms, a range of molar ratios, a range of temperatures, a range of times, and so forth. When Applicants disclose or claim a range of any type, Applicants' intent is to disclose or claim individually each possible number that such a range could reasonably encompass, including end points of the range as well as any sub-ranges and combinations of sub-ranges encompassed therein. For example, when the Applicants disclose or claim a chemical moiety having a certain number of carbon atoms, Applicants' intent is to disclose or claim individually every possible number that such a range could encompass, consistent with the disclosure herein. For example, the disclosure that a moiety is a $C_1$ to $C_{18}$ hydrocarbyl group, or in alternative language a hydrocarbyl group having up to 18 carbon atoms, as used herein, refers to a moiety that can be selected independently from a hydrocarbyl group having 1, 2, 3, 4, 5, 6, 7, 8, 9, 10, 11, 12, 13, 14, 15, 16, 17, or 18 carbon atoms, as well as any range between these two numbers (for example, a $C_1$ to $C_8$ hydrocarbyl group), and also including any combination of ranges between these two numbers (for example, a $C_2$ to $C_4$ and a $C_{12}$ to $C_{16}$ hydrocarbyl group).

Similarly, another representative example follows for the stereoselectivity of an ansa-metallocene compound (e.g., the rac:meso molar ratio) provided in one aspect of this invention. By a disclosure that the rac:meso molar ratio of the ansa-metallocene compound can be in a range from 4:1 to about 100:1, Applicants intend to recite that the molar ratio can be 4:1, about 5:1, about 6:1, about 7:1, about 8:1, about 9:1, about 10:1, about 12:1, about 15:1, about 20:1, about 25:1, about 35:1, about 45:1, about 50:1, about 60:1, about 75:1, about 90:1, about 95:1, or about 100:1. Additionally, the rac:meso molar ratio can be within any range from 4:1 to about 100:1 (for example, from about 5:1 to about 20:1), and this also includes any combination of ranges between 4:1 and about 100:1 (for example, the molar ratio is in a range from 4:1 to about 10:1, or from about 20:1 to about 75:1). Likewise, all other ranges disclosed herein should be interpreted in a manner similar to these two examples.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants may be unaware of at the time of the filing of the application. Further, Applicants reserve the right to proviso out or exclude any individual substituents, analogs, compounds, ligands, structures, or groups thereof, or any members of a claimed group, if for any reason Applicants choose to claim less than the full measure of the disclosure, for example, to account for a reference that Applicants may be unaware of at the time of the filing of the application.

The terms "a," "an," and "the" are intended to include plural alternatives, e.g., at least one, unless otherwise specified. For instance, the disclosure of "a solvent" or "a base" is meant to encompass one, or mixtures or combinations of more than one, solvent or base, respectively.

While compositions and methods are described in terms of "comprising" various components or steps, the compositions and methods can also "consist essentially of" or "consist of" the various components or steps. For example, a method of making an ansa-metallocene compound of the present invention from a compound having formula (IV) can comprise; alternatively, can consist essentially of; or alternatively, can consist of; step (a) and step (b).

The following abbreviations are used in this disclosure:
Bu—n-butyl (also n-Bu)
Et—ethyl
i-Pr—iso-propyl
Me—methyl
Ph—phenyl
Pr—n-propyl
t-Bu—tert-butyl or t-butyl
THF—tetrahydrofuran

DETAILED DESCRIPTION OF THE INVENTION

The present invention is directed generally to processes for the stereo-enriched synthesis of ansa-metallocene compounds.

Synthesis of a Stereo-Enriched Ansa-Metallocene

In accordance with the present invention, methods of making stereo-enriched ansa-metallocene compounds having the formula:

$$E(CpR^A{}_n)_2M(NR_2)_m \quad (I), \text{ are disclosed.}$$

Such compounds can be used in catalyst compositions, for example, in the polymerization of olefins to form homopolymers, copolymers, terpolymers, and the like.

In accordance with one aspect of this invention, a method of making a stereo-enriched ansa-metallocene compound having formula (I) is provided and, in this aspect, the method comprises:

reacting a compound having formula (II):

$$E(CpR^A{}_n)_2M^A{}_2 \quad (II)$$

with an unchelated amine compound having formula (III):

$$M(NR_2)_m X_p L_q \quad (III).$$

As noted above, this method applies only to compounds (e.g., compounds having formula (I)) that exhibit chirality, i.e., compounds having prochiral Cp groups.

In this method of making a stereo-enriched ansa-metallocene compound having formula (I), M is Ti, Zr, Hf, Cr, Sc, Y, La, or a lanthanide;

Cp is a cyclopentadienyl, indenyl, or fluorenyl group;

E is a substituted or unsubstituted bridging chain of 3 to 8 carbon atoms or 2 to 8 silicon, germanium, or tin atoms, wherein any substituents on atoms of the bridging chain independently are H or a hydrocarbyl group having up to 18 carbon atoms;

each R independently is H, a hydrocarbyl, hydrocarbylsilyl, hydrocarbylamino, or hydrocarbyloxide group having up to 18 carbon atoms, or each $NR_2$ group is a heterocyclic group having up to 18 carbon atoms;

each $R^A$ independently is H or a hydrocarbyl, hydrocarbylsilyl, hydrocarbylamino, or hydrocarbyloxide group having up to 18 carbon atoms;

m is 2, p is 2, and q is 0, 1, or 2 when M is Ti, Zr, or Hf;

m is 1, p is 2, and q is 0, 1, 2, or 3 when M is Cr, Sc, Y, La, or a lanthanide;

n is 0, 1, 2, 3, or 4 when Cp is an indenyl group;

n is 1, 2, 3, or 4 when Cp is a cyclopentadienyl or a fluorenyl group;

each $M^A$ independently is Li, Na, K, $SiR^B{}_3$, $AlR^B{}_2$, $SnR^B{}_3$, ½ Mg, ½ Zn, MgX, or ZnX, wherein $R^B$ is an alkyl group having up to 18 carbon atoms;

each X independently is triflate, a halide, or a sulfonate; and each L independently is a neutral Lewis base donor ligand.

Unless otherwise specified, formulas (I), (II), and (III) above, any other structural formulas disclosed herein, and any species or compound disclosed herein are not designed to show stereochemistry or isomeric positioning of the different moieties (e.g., these formulas are not intended to display cis or trans isomers, or R or S diastereoisomers), although such compounds are contemplated and encompassed by these formulas and/or structures.

Hydrocarbyl is used herein to specify a hydrocarbon radical group that includes, but is not limited to, aryl, alkyl, cycloalkyl, alkenyl, cycloalkenyl, cycloalkadienyl, alkynyl, aralkyl, aralkenyl, aralkynyl, and the like, and includes all substituted, unsubstituted, linear, and/or branched derivatives thereof. Unless otherwise specified, the hydrocarbyl groups of this invention typically comprise up to about 18 carbon atoms. In another aspect, hydrocarbyl groups can have up to 12 carbon atoms, for instance, up to 10 carbon atoms, up to 8 carbon atoms, or up to 6 carbon atoms. A hydrocarbyloxide group, therefore, is used generically to include alkoxide, aryloxide, and -(alkyl or aryl)-O-(alkyl or aryl) groups, and these groups can comprise up to about 18 carbon atoms. Illustrative and non-limiting examples of alkoxide and aryloxide groups (i.e., hydrocarbyloxide groups) include methoxy, ethoxy, propoxy, butoxy, phenoxy, substituted phenoxy, and the like. The term hydrocarbylamino group is used generically to refer collectively to alkylamino, arylamino, dialkylamino, diarylamino, and -(alkyl or aryl)-N-(alkyl or aryl) groups, and the like. Unless otherwise specified, the hydrocarbylamino groups of this invention comprise up to about 18 carbon atoms. Hydrocarbylsilyl groups include, but are not limited to, alkylsilyl groups, alkenylsilyl groups, arylsilyl groups, arylalkylsilyl groups, and the like, which have up to about 18 carbon atoms. For example, illustrative hydrocarbylsilyl groups can include trimethylsilyl and phenyloctylsilyl. These hydrocarbyloxide, hydrocarbylamino, and hydrocarbylsilyl groups can have up to 12 carbon atoms; alternatively, up to 10 carbon atoms; or alternatively, up to 8 carbon atoms, in other aspects of the present invention.

Unless otherwise specified, alkyl groups and alkenyl groups described herein are intended to include all structural isomers, linear or branched, of a given moiety; for example, all enantiomers and all diastereomers are included within this definition. As an example, unless otherwise specified, the term propyl is meant to include n-propyl and iso-propyl, while the term butyl is meant to include n-butyl, iso-butyl, t-butyl, sec-butyl, and so forth. For instance, non-limiting examples of octyl isomers include 2-ethyl hexyl and neooctyl. Suitable examples of alkyl groups which can be employed in the present invention include, but are not limited to, methyl, ethyl, propyl, butyl, pentyl, hexyl, heptyl, octyl, nonyl, decyl, and the like. Illustrative examples of alkenyl groups within the scope of the present invention include, but are not limited to, ethenyl, propenyl, butenyl, pentenyl, hexenyl, heptenyl, octenyl, nonenyl, decenyl, and the like. The alkenyl group can be a terminal alkenyl group, but this is not a requirement. For instance, specific alkenyl group substituents can include, but are not limited to, 3-butenyl, 4-pentenyl, 5-hexenyl, 6-heptenyl, 7-octenyl, 3-methyl-3-butenyl, 4-methyl-3-pentenyl, 1,1-dimethyl-3-butenyl, 1,1-dimethyl-4-pentenyl, and the like.

In this disclosure, aryl is meant to include aryl and arylalkyl groups, and these include, but are not limited to, phenyl, alkyl-substituted phenyl, naphthyl, alkyl-substituted naphthyl, phenyl-substituted alkyl, naphthyl-substituted alkyl, and the like. Hence, non-limiting examples of such "aryl" moieties that can be used in the present invention include phenyl, tolyl, benzyl, dimethylphenyl, trimethylphenyl, phenylethyl, phenylpropyl, phenylbutyl, propyl-2-phenylethyl, and the like. Unless otherwise specified, any substituted aryl moiety used herein is meant to include all regioisomers; for example, the term tolyl is meant to include any possible substituent position, that is, ortho, meta, or para.

In the method of making a stereo-enriched ansa-metallocene compound having formula (I) from the compound having formula (II) and the unchelated amine compound having formula (III), M is Ti, Zr, Hf, Cr, Sc, Y, La, or a lanthanide. In one aspect of this invention, M is Ti, Zr, Hf, or Cr. In another aspect, M is Sc, Y, or La. In still another aspect, M is a lanthanide. Yet, in some aspects disclosed herein, M is Ti, Zr, Hf, Cr, or a lanthanide; alternatively, M is Ti, Zr, Hf, or Cr; alternatively, M is Ti, Zr, or Hf; alternatively, M is Ti; alternatively, M is Zr; or alternatively, M is Hf.

When M is Ti, Zr, or Hf, m is 2, p is 2, and q is 0, 1, or 2. However, when M is Cr, Sc, Y, La, or a lanthanide, m is 1, p is 2, and q is 0, 1, 2, or 3.

Cp in formulas (I) and (II) is a cyclopentadienyl, indenyl, or fluorenyl group. In an aspect of this invention, Cp is an indenyl group. When Cp is an indenyl group, n is 0, 1, 2, 3, or 4. Hence, when n is equal to 0, Cp can be an unsubstituted indenyl group, i.e., other than E. When Cp is a cyclopentadienyl or a fluorenyl group, n is 1, 2, 3, or 4.

E is a substituted or unsubstituted bridging chain of 3 to 8 carbon atoms or 2 to 8 silicon, germanium, or tin atoms. For example, E can be a substituted or unsubstituted bridging chain of 3 to 8 carbon atoms, of 3 to 6 carbon atoms, of 3 carbon atoms, or of 4 carbons atoms. Alternatively, E can be a substituted or unsubstituted bridging chain of 2 to 8 silicon, germanium, or tin atoms, of 2 to 6 silicon, germanium, or tin atoms, of 2 to 4 silicon, germanium, or tin atoms, or of 2 silicon atoms. Any substituents on atoms of the bridging chain independently are H or a hydrocarbyl group having up to 18 carbon atoms or, alternatively, having up to 12 carbon atoms. Suitable substituents can include, but are not limited to, H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, or benzyl. In one aspect, the substituents independently can be H, methyl, ethyl, propyl, butyl, pentyl, hexyl, allyl, butenyl, pentenyl, hexenyl, phenyl, or benzyl. In another aspect, the substituents independently can be methyl, ethyl, propyl, butyl, allyl, butenyl, pentenyl, or phenyl.

In accordance with one aspect of this invention, E is a bridging chain having the formula $-(CR^{10A}R^{10B})_u-$, wherein u is an integer from 3 to 8 (e.g., u is 3, 4, 5, or 6), and $R^{10A}$ and $R^{10B}$ are independently H or a hydrocarbyl group having up to 18 carbon atoms; alternatively, up to 12 carbon atoms; or alternatively, up to 8 carbon atoms. It is contemplated that $R^{10A}$ and $R^{10B}$ independently can be H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, or benzyl; alternatively, H, methyl, ethyl, propyl, butyl, allyl, butenyl, pentenyl, phenyl, or benzyl; or alternatively, H, methyl, ethyl, propyl, or butyl. In some aspects, u is 3, 4, 5, or 6, and $R^{10A}$ and $R^{10B}$ both are H, or methyl, or ethyl, or propyl, or butyl, or allyl, or butenyl, or pentenyl, or phenyl, or benzyl.

In accordance with another aspect of this invention, E is a bridging chain having the formula $-(SiR^{11A}R^{11B})_v-$, wherein v is an integer from 2 to 8 (e.g., v is 2, 3, 4, 5, or 6), and $R^{11A}$ and $R^{11B}$ are independently H or a hydrocarbyl group having up to 18 carbon atoms; alternatively, up to 12 carbon atoms; or alternatively, up to 8 carbon atoms. It is contemplated that $R^{11A}$ and $R^{11B}$ independently can be H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, or benzyl; alternatively, H, methyl, ethyl, propyl, butyl, allyl, butenyl, pentenyl, phenyl, or benzyl; or alternatively, H, methyl, ethyl, propyl, or butyl. In some aspects, v is 2, 3, 4, 5, or 6 (e.g., v is 2), and $R^{11A}$ and $R^{11B}$ both are H, or methyl, or ethyl, or propyl, or butyl, or allyl, or butenyl, or pentenyl, or phenyl, or benzyl.

In formulas (I) and (III), each R independently is H, a hydrocarbyl, hydrocarbylsilyl, hydrocarbylamino, or hydrocarbyloxide group, or each $NR_2$ group is a heterocyclic group. The hydrocarbyl group, the hydrocarbyloxide group, the hydrocarbylamino group, and the hydrocarbylsilyl group can have up to 18 carbon atoms or, alternatively, up to 12 carbon atoms. In some aspects, each R independently can be H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, or trimethylsilyl, while in other aspects, each R independently can be methyl, ethyl, propyl, butyl, pentyl, hexyl, heptyl, octyl, nonyl, decyl, or trimethylsilyl. For example, each R independently can be methyl, ethyl, or propyl in some aspects disclosed herein.

Each $NR_2$ group in formulas (I) and (III) can be a heterocyclic group having up to 18 carbon atoms; alternatively, up to 12 carbon atoms; or alternatively, up to 8 carbon atoms. Heterocyclic groups can include heterocycloalkyl and heterocycloalkenyl moieties and, often, these heterocyclic moieties can be 3-membered, 4-membered, 5-membered, 6-membered, or 7-membered rings.

In formulas (I) and (II), each $R^A$ independently is H or a hydrocarbyl, hydrocarbylsilyl, hydrocarbylamino, or hydrocarbyloxide group having up to 18 carbon atoms or, alternatively, having up to 12 carbon atoms. In one aspect of the present invention, each $R^A$ independently is H or an alkyl, alkenyl, or aryl group having up to 12 carbon atoms. Accordingly, each $R^A$ independently can be H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, or benzyl. In another aspect, each $R^A$ independently is H, t-butyl, or trimethylsilyl; alternatively, $R^A$ is H; alternatively, $R^A$ is t-butyl; or alternatively, $R^A$ is trimethylsilyl.

Each $R^A$ substituent, independently, can be different. For instance, Cp can have both a methyl substituent and a butyl substituent. However, each $(CpR^A_n)$ group must have the same selection for Cp and for each $R^A$ in order to exhibit stereoisomerism.

Each X in formula (III) independently is triflate, a halide, or a sulfonate. In one aspect, X can be a sulfonate having the formula $SO_3R^C$, wherein $R^C$ is an alkyl or aryl group having up to 18 carbon atoms or, alternatively, up to 12 carbon atoms. For instance, $R^C$ can be methyl, ethyl, propyl, butyl, pentyl, hexyl, heptyl, octyl, nonyl, or decyl, and the like. In another aspect, each X independently can be a halide, or each X independently can be Cl or Br. Yet, in another aspect, each X can be Cl; alternatively, each X can be F; alternatively, each X can be Br; or alternatively, each X can be I.

Each $M^A$ in formula (II) independently can be Li, Na, K, $SiR^B_3$, $AlR^B_2$, $SnR^B_3$, ½ Mg, ½ Zn, MgX, or ZnX, wherein $R^B$ is an alkyl group having up to 18 carbon atoms or, alternatively, up to 12 carbon atoms. Thus, $R^B$ can be methyl, ethyl, propyl, butyl, pentyl, hexyl, heptyl, octyl, nonyl, or decyl, and the like. In some aspects, $R^B$ is an alkyl group having up to 6 carbon atoms. Regarding MgX and ZnX, as noted above, X can be triflate, a halide, or a sulfonate. In aspects of this invention, each $M^A$ independently can be Li, Na, K, ½ Mg, or ½ Zn; alternatively, Li, Na, or K; alternatively, Li; alternatively, Na; or alternatively, K.

In formula (III), each L independently is a neutral Lewis base donor ligand. For instance, each L independently can be THF, acetonitrile, a pyridine, an ether, a thioether, an amine, an isocyanide, or a phosphine, and the like, but is not limited thereto. L can comprise any functional group capable of donating electrons to a metal. In some aspects, each L independently can be THF or acetonitrile. In other aspects, each L independently can be a pyridine; alternatively, an ether; alternatively, a thioether; alternatively, an amine; alternatively, an isocyanide; or alternatively, a phosphine. When M is Ti, Zr, or Hf, q is 0, 1, or 2; when M is Cr, Sc, Y, La, or a lanthanide, q is 0, 1, 2, or 3.

In accordance with an aspect of this invention, in formulas (I), (II), and (III), M is Ti, Zr, or Hf; Cp is an indenyl group; m is 2; p is 2; q is 2; n is 0; each R independently is methyl, ethyl, propyl, butyl, pentyl, hexyl, heptyl, octyl, nonyl, decyl, or trimethylsilyl; each $M^A$ independently is Li, Na, or K; and each X independently is F, Cl, Br, or I. In these and other aspects, E can be a substituted or unsubstituted bridging chain of 3 to 6 carbon atoms or 2 to 6 silicon atoms. In a further aspect, E can be a bridging chain having the formula —$(CR^{10A}R^{10B})_u$— or the formula —$(SiR^{11A}R^{11B})_v$—, where u is 3, 4, 5, or 6 (e.g., u is 4), v is 2, 3, 4, 5, or 6 (e.g., v is 3), and $R^{10A}$, $R^{10B}$, $R^{11A}$, and $R^{11B}$ are independently H, methyl, ethyl, propyl, butyl, allyl, butenyl, pentenyl, phenyl, or benzyl (e.g., H and/or methyl).

In accordance with another aspect of this invention, in formulas (I), (II), and (III), M is Ti, Zr, or Hf; Cp is a cyclopentadienyl or a fluorenyl group; m is 2; p is 2; q is 2; n is 1 or 2; each $R^A$ independently is H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, or tolyl; each R independently is methyl, ethyl, propyl, butyl, pentyl, hexyl, heptyl, octyl, nonyl, decyl, or trimethylsilyl; each $M^A$ independently is Li, Na, or K; and each X independently is F, Cl, Br, or I. In these and other aspects, E can be a substituted or unsubstituted bridging chain of 3 to 6 carbon atoms or 2 to 6 silicon atoms. In a further aspect, E can be a bridging chain having the formula —$(CR^{10A}R^{10B})_u$— or the formula —$(SiR^{11A}R^{11B})_v$—, where u is 3, 4, 5, or 6 (e.g., u is 4), v is 2, 3, 4, 5, or 6 (e.g., v is 3), and $R^{10A}$, $R^{10B}$, $R^{11A}$, and $R^{11B}$ are independently H, methyl, ethyl, propyl, butyl, allyl, butenyl, pentenyl, phenyl, or benzyl (e.g., H and/or methyl).

A non-limiting example of a stereo-enriched ansa-metallocene compound having formula (I) that can be produced using the methods described herein includes, but is not limited to, the following:

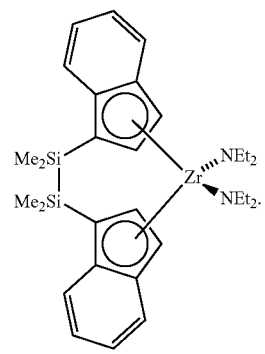

A non-limiting example of a compound having formula (II) that can be employed in the methods described herein includes, but is not limited to, the following:

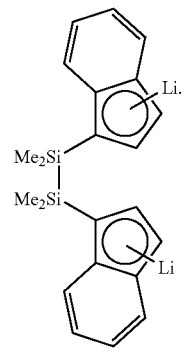

Non-limiting examples of unchelated amine compounds having formula (III) that can be employed in the methods described herein include, but are not limited to, the following:

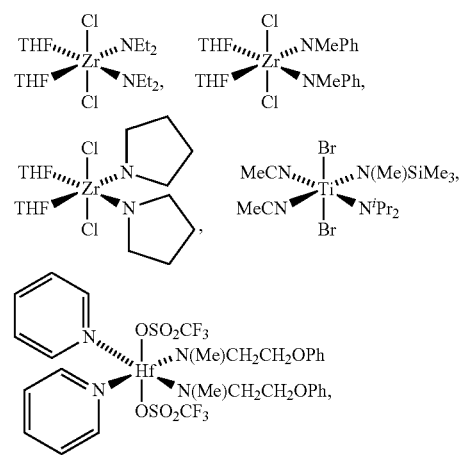

and the like, or any combination thereof.

In accordance with aspects of the method of making a stereo-enriched ansa-metallocene compound having formula (I), the reaction between the compound having formula (II) and the unchelated amine compound having formula (III) can be conducted in the presence of a solvent. The solvent can comprise one or more of an ether, an aliphatic hydrocarbon, an aromatic hydrocarbon, including combinations thereof.

In an aspect, the solvent can comprise an ether. Suitable ethers can be a $C_4$ to $C_{20}$ ether; alternatively, a $C_4$ to $C_{10}$ ether; or alternatively, a $C_4$ to $C_8$ ether. The solvent can comprise, for example, diethyl ether, diisopropyl ether, di-n-propyl ether, di-n-butyl ether, diphenyl ether, methyl ethyl ether, methyl t-butyl ether, dihydrofuran, tetrahydrofuran (THF), 1,2-dimethoxyethane, and the like, or any combination of more than one of these materials.

Aliphatic hydrocarbons which may be useful as a solvent include $C_5$ to $C_{20}$ hydrocarbons, or alternatively, $C_5$ to $C_{10}$ hydrocarbons, and may be cyclic or acyclic and include linear or branched isomers, unless otherwise specified. Non-limiting examples of suitable acyclic aliphatic solvents include pentane, hexane, heptane, octane, and the like, and combinations thereof. Non-limiting examples of suitable cyclic aliphatic solvents include cyclopentane, cyclohexane, methyl cyclopentane, methyl cyclohexane, and the like, and combinations thereof, Aromatic hydrocarbons which may be useful as a solvent include $C_6$ to $C_{20}$ aromatic hydrocarbons; or alternatively, $C_6$ to $C_{10}$ aromatic hydrocarbons. Non-limiting examples of suitable aromatic hydrocarbons include benzene, toluene, xylene (including ortho-xylene, meta-xylene, para-xylene, or mixtures thereof), and ethylbenzene, or combinations thereof. In one aspect, the solvent employed can comprise pentane, hexane, heptane, octane, cyclopentane, cyclohexane, methyl cyclopentane, methyl cyclohexane, benzene, toluene, xylene, ethylbenzene, or combinations of two or more of these solvents.

In accordance with aspects of this invention, the solvent can comprise diethyl ether, THF, pentane, hexane, heptane, octane, cyclopentane, cyclohexane, methyl cyclopentane, methyl cyclohexane, benzene, toluene, xylene, or any combination thereof.

In accordance with another aspect of this invention, the molar ratio of the compound having formula (II) to the unchelated amine compound having formula (III) can be in a range from about 1.5:1 to about 1:1.5, such as, for example, from about 1.4:1 to about 1:1.4, from about 1.3:1 to about 1:1.3, or from about 1.2:1 to about 1:1.2. Additionally, the molar ratio of the compound having formula (II) to the unchelated amine compound having formula (III) can be in a range from about 1.1:1 to about 1:1.1, or from about 1.05:1 to about 1:1.05, in other aspects disclosed herein.

The reaction between the compound having formula (II) and the unchelated amine compound having formula (III) can be conducted at a variety of temperatures. For instance, the reaction can be conducted at a temperature in a range from about −80° C. to about 70° C.; alternatively, from about −60° C. to about 60° C.; alternatively, from about −30° C. to about 50° C.; alternatively, from about −10° C. to about 40° C.; or alternatively, from about −10° C. to about 25° C.

The appropriate contact or reaction time in the methods of this invention can depend greatly upon the temperature and the reactant concentrations that are selected, among other variables. Often, the total reaction time is from about 1 minute to about 24 hours, from about 2 minutes to about 20 hours, from about 3 minutes to about 18 hours, from about 4 minutes to about 12 hours, or from about 5 minutes to about 8 hours.

The temperature at which the reaction components are initially combined can be the same as, or different from, the temperature at which the reaction is allowed to proceed or run for its duration. As an illustrative example, the compound having formula (II) and the unchelated amine compound having formula (III) can be combined initially at temperature T1 and, after combining, the temperature can be increased to a temperature T2 for the remainder of the contacting or reacting to form the stereo-enriched ansa-metallocene compound having formula (I). In an aspect of this invention, the compound having formula (II) and the unchelated amine compound having formula (III) can be combined initially at temperature in a range from about −80° C. to about 25° C.; alternatively, from about −70° C. to about 20° C.; alternatively, from about −60° C. to about 15° C.; alternatively, from about −50° C. to about 10° C.; or alternatively, from about −40° C. to about 5° C. In these and other aspects, after the initial combining, the temperature can be changed to another temperature to initiate and/or complete the reaction, such as a temperature in the 20° C. to 120° C. range, a temperature in the 20° C. to 80° C. range, or a temperature in the 20° C. to 60° C. range. As an example, the compound having formula (II) and the unchelated amine compound having formula (III) can be contacted or combined initially at a temperature of less than about −40° C., and then subsequently heated to a temperature in a range from about 20° C. to about 120° C., or from about 20° C. to about 50° C., to initiate and/or complete the reaction.

The initial combining time can be quite rapid and, often, the initial combining time of the reaction components is less than about 10 minutes, less than about 5 minutes, or less than about 3 minutes. In some aspects, the reaction components are initially contacted in a time period of less than about 1 minute, while in other aspects, in a time period of less than about 30 seconds.

Synthesis methods of this invention can produce a stereo-enriched ansa-metallocene compound having a 4:1 or greater isomer ratio. Thus, the molar ratio of the rac isomer to the meso isomer of the ansa-metallocene compound having formula (I) can be greater than 4:1. In some aspects, the rac:meso isomer ratio is greater than about 5:1, while in other aspects, the rac:meso isomer ratio is greater than about 6:1; alternatively, greater than about 7:1; alternatively, greater than about 8:1; alternatively, greater than about 9:1, alternatively, greater than about 10:1; or alternatively, greater than about 20:1. In another aspect, the rac:meso isomer ratio can fall within a range from 4:1 to about 100:1, such as, for example, from about 5:1 to about 90:1, from about 6:1 to about 75:1, from about 8:1 to about 50:1, or from about 10:1 to about 40:1.

Stated another way, the rac:meso stereoselectivity of the methods of making a stereo-enriched ansa-metallocene compound having formula (I) in accordance with this invention can be greater than 4:1, or greater than about 5:1, or greater than about 7:1, or greater than about 10:1, or greater than about 15:1, or greater than about 20:1. Additionally or alternatively, the rac:meso stereoselectivity of the methods disclosed herein for making a stereo-enriched ansa-metallocene compound having formula (I) can be in a range from 4:1 to about 100:1, or from about 5:1 to about 90:1, or from about 5:1 to about 75:1, or from about 5:1 to about 50:1, or from about 5:1 to about 25:1.

In some aspects, the methods of making a stereo-enriched ansa-metallocene compound having formula (I) can be methods of making a rac-ansa-metallocene compound having formula (I), wherein the amount of the meso isomer produced in the method is less than 25% of the amount of the rac isomer produced. Alternatively, the amount of the meso isomer produced in the method of making a rac-ansa-metallocene compound having formula (I) can be less than about 20%, or less than about 15%, or less than about 10%, or less than about 5%, or less than about 2%, based on the amount of the rac isomer produced.

In another aspect, the method of making a stereo-enriched ansa-metallocene compound having formula (I) can have a yield of greater than about 80%. This yield includes all isomers having formula (I). Yet, in another aspect, the yield of the ansa-metallocene compound having formula (I) can be greater than about 85%, greater than about 90%, or greater than about 95%.

Synthesis of a Stereo-Enriched Ansa-Metallocene from a Rac/Meso Bridged Ligand

In accordance with another aspect of the present invention, a method of making a stereo-enriched ansa-metallocene compound having formula (I) is provided and, in this aspect, the starting material is a bridged ligand. The bridged ligand can be a mixture of rac and meso isomers. This method comprises:

(a) contacting a compound having formula (IV):

$$E(CpR^A{}_n)_2 \qquad (IV)$$

with a strong base in the presence of a solvent to form an intermediate mixture comprising a dianion of the compound having formula (IV); and (b) contacting the intermediate mixture comprising the dianion of the compound having formula (IV) with an unchelated amine compound having formula (III):

$$M(NR_2)_m X_p L_q \qquad (III).$$

In this method of synthesis using a bridged ligand, M, Cp, E, R, $R^A$, m, n, p, q, X, and L can be any of the selections described above in relation to the method of synthesizing a stereo-enriched ansa-metallocene from the compound having formula (II) and the unchelated amine compound having formula (III). Additionally, as would be recognized by those of skill in the art, this method applies only to compounds that exhibit chirality, i.e., compounds having prochiral Cp groups.

It is contemplated in aspects of this invention that, in formulas (I), (III), and (IV), M is Ti, Zr, or Hf; Cp is an indenyl group; m is 2; p is 2; q is 2; n is 0; each R independently is methyl, ethyl, propyl, butyl, pentyl, hexyl, heptyl, octyl, nonyl, decyl, or trimethylsilyl; and each X independently is F, Cl, Br, or I. In these and other aspects, E can be a substituted or unsubstituted bridging chain of 3 to 6 carbon atoms or 2 to 6 silicon atoms. In a further aspect, E can be a bridging chain having the formula $-(CR^{10A}R^{10B})_u-$ or the formula $-(SiR^{11A}R^{11B})_v-$, where u is 3, 4, 5, or 6 (e.g., u is 4), v is 2, 3, 4, 5, or 6 (e.g., v is 3), and $R^{10A}$, $R^{10B}$, $R^{11A}$, and $R^{11B}$ are independently H, methyl, ethyl, propyl, butyl, allyl, butenyl, pentenyl, phenyl, or benzyl (e.g., H and/or methyl).

It is also contemplated in aspects of this invention that, in formulas (I), (III), and (IV), M is Ti, Zr, or Hf; Cp is a cyclopentadienyl or a fluorenyl group; m is 2; p is 2; q is 2; n is 1 or 2; each $R^A$ independently is H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, or tolyl; each R independently is methyl, ethyl, propyl, butyl, pentyl, hexyl, heptyl, octyl, nonyl, decyl, or trimethylsilyl; and each X independently is F, Cl, Br, or I. In these and other aspects, E can be a substituted or unsubstituted bridging chain of 3 to 6 carbon atoms or 2 to 6 silicon atoms. In a further aspect, E can be a bridging chain having the formula $-(CR^{10A}R^{10B})_u-$ or the formula $-(SiR^{11A}R^{11B})_v-$, where u is 3, 4, 5, or 6 (e.g., u is 4), v is 2, 3, 4, 5, or 6 (e.g., v is 3), and $R^{10A}$, $R^{10B}$, $R^{11A}$, and $R^{11B}$ are independently H, methyl, ethyl, propyl, butyl, allyl, butenyl, pentenyl, phenyl, or benzyl (e.g., H and/or methyl).

In accordance with aspects of the method of making a stereo-enriched ansa-metallocene having formula (I) from a bridged ligand, the strong base can comprise a lithium, sodium, or potassium atom, or a combination thereof. For example, the strong base can comprise an alkyl lithium, an alkyl sodium, an alkyl potassium, lithium hydride, sodium hydride, potassium hydride, or any combination thereof. Illustrative and non-limiting examples of suitable materials that can be employed as the strong base can include MeLi, n-BuLi, t-BuLi, n-hexylLi, $LiCH_2SiMe_3$, $LiCH_2Ph$, $LiCH_2CMe_3$, Lilt NaH, KH, or any combination of these materials. Applicants contemplate that the strong base can comprise one or more than one of these compounds.

The solvent in this method of synthesis from a bridged ligand can be any of the solvent selections described above in relation to the method of synthesizing a stereo-enriched ansa-metallocene from the compound having formula (II) and the unchelated amine compound having formula (III). For instance, the solvent can comprise one or more of an ether, an aliphatic hydrocarbon, an aromatic hydrocarbon, including combinations thereof. Hence, the solvent can comprise an ether, suitable examples of which include, but are not limited to, diethyl ether, diisopropyl ether, di-n-propyl ether, di-n-butyl ether, diphenyl ether, methyl ethyl ether, methyl t-butyl ether, dihydrofuran, tetrahydrofuran (THF), 1,2-dimethoxyethane, and the like, or any combination of two or more of these materials. Aliphatic and/or aromatic hydrocarbons can be employed, and non-limiting examples include pentane, hexane, heptane, octane, cyclopentane, cyclohexane, methyl cyclopentane, methyl cyclohexane, benzene, toluene, xylene, and the like, or combinations thereof.

In accordance with one aspect of this invention, the molar ratio of the compound having formula (IV) to the unchelated amine compound having formula (III) can be in a range from about 1.5:1 to about 1:1.5, such as, for example, from about 1.4:1 to about 1:1.4, from about 1.3:1 to about 1:1.3, or from about 1.2:1 to about 1:1.2. Additionally, the molar ratio of the compound having formula (IV) to the unchelated amine compound having formula (III) can be in a range from about 1.1:1 to about 1:1.1, or from about 1.05:1 to about 1:1.05, in other aspects disclosed herein.

In accordance with another aspect of this invention, the molar ratio of the strong base to the compound having formula (IV) is in a range from about 3:1 to about 1.5:1. For instance, the molar ratio can be in a range from about 2.8:1 to about 1.8:1; alternatively, from about 2.6:1 to about 1.8:1; alternatively, from about 2.4:1 to about 1.8:1, alternatively, from about 2.2:1 to about 1.8:1; or alternatively, from about 2.1:1 to about 1.9:1.

As with the contacting or reacting of the compound having formula (II) and the unchelated amine compound having formula (III), steps (a) and (b) in this method of making a stereo-enriched ansa-metallocene having formula (I) from a bridged ligand can be conducted, independently, over the same variety of temperatures and times. For instance, step (a) and step (b) can be conducted, independently, at a temperature in a range from about −80° C. to about 70° C., or from about −10° C. to about 40° C., for a time period of from about 1 minute to about 24 hours, or from about 5 minutes to about 8 hours. Additionally, the components of step (a) and step (b) can be contacted or combined initially at a temperature in a range from about −80° C. to about 10° C., or from about −70° C. to about −10° C. Then, the temperature can be increased to a temperature in a range from about 20° C. to about 120° C., or from about 20° C. to about 60° C., to complete the respective step in the method. The initial combining or initial contacting can performed rapidly, for instance, in less than about 5 minutes, less than 3 minutes, or less than about 1 minute. Additionally, in some aspects, the dianion of the compound having formula (IV) formed in step (a) may be purified and/or isolated prior to use in step (b).

In the method of synthesizing a stereo-enriched ansa-metallocene compound having formula (I) from the compound having formula (IV) and the unchelated amine compound having formula (III), the stereo-enriched ansa-metallocene compound can be formed in a 4:1 or greater isomer ratio, e.g., a molar ratio of the rac isomer to the meso isomer of greater than 4:1. In accordance with others aspects, rac:meso isomer ratios of greater than about 5:1, greater than about 6:1, greater than about 7:1, greater than about 8:1, greater than about 9:1, greater than about 10:1, or greater than about 15:1, can be obtained. In another aspect, the rac:meso isomer ratio can fall within a range from 4:1 to about 100:1, including, for example, from about 5:1 to about 90:1, from about 6:1 to about 75:1, from about 8:1 to about 50:1, or from about 10:1 to about 40:1.

Stated another way, the rac:meso stereoselectivity of the method of synthesizing a stereo-enriched ansa-metallocene compound having formula (I), from the compound having formula (IV) and the unchelated amine compound having formula (III), in accordance with this invention can be greater than 4:1, or greater than about 5:1, or greater than about 7:1, or greater than about 10:1, or greater than about 15:1, or greater than about 20:1. In another aspect, the rac:meso stereoselectivity of this method can be in a range from 4:1 to about 100:1, or from about 5:1 to about 90:1, or from about 5:1 to about 75:1, or from about 5:1 to about 50:1, or from about 5:1 to about 25:1.

In some aspects, the method of synthesizing a stereo-enriched ansa-metallocene compound having formula (I), from the compound having formula (IV) and the unchelated amine compound having formula (III), can be a method of making a rac-ansa-metallocene compound having formula (I), wherein the amount of the meso isomer produced in the method is less than 25% of the amount of the rac isomer produced; alternatively, less than about 20%; alternatively, less than about 15%; alternatively, less than about 10%; or alternatively, less than about 5%.

In another aspect, the method of making a stereo-enriched ansa-metallocene compound having formula (I) can have a yield of greater than about 80%. This yield includes all isomers having formula (I). Yet, in another aspect, the yield of the ansa-metallocene compound having formula (I) can be greater than about 85%, greater than about 90%, or greater than about 95%.

Subsequent Synthesis and Purification

Optionally, the disclosed methods of making a stereo-enriched ansa-metallocene compound having formula (I) can further comprise a step of converting the stereo-enriched ansa-metallocene compound having formula (I) to a compound having formula (V):

It is contemplated that the rac:meso isomer ratio of the metallocene compound having formula (I) will be maintained once converted to the compound having formula (V). Hence, the ansa-metallocene compound having formula (V) can have any rac:meso isomer ratio disclosed herein, e.g., greater than 4:1, or greater than about 5:1, or greater than about 8:1, or greater than about 10:1, and so forth.

Any suitable method for converting the stereo-enriched ansa-metallocene compound having formula (I) to a compound having formula (V) can be employed. One suitable procedure is described in U.S. Pat. No. 6,207,608, the disclosure of which is incorporated herein by reference in its entirety. U.S. Pat. No. 6,207,608 uses $Me_2NH \cdot HCl$ as a reactant.

M, Cp, E, $R^A$, m, and n in formula (V) can be any of the selections described above in relation to the method of synthesizing a stereo-enriched ansa-metallocene from the compound having formula (II) and the unchelated amine compound having formula (III). For instance, m can be 2 and, additionally or alternatively, n can be 0.

In another aspect, in formula (V), M is Ti, Zr, or Hf; Cp is an indenyl group; m is 2; n is 0; and E is a substituted or unsubstituted bridging chain of 3 to 6 carbon atoms or 2 to 6 silicon atoms. In a further aspect, E can be a bridging chain having the formula $-(CR^{10A}R^{10B})_u-$ or the formula $-(SiR^{11A}R^{11B})_v-$, where u is 3, 4, 5, or 6 (e.g., u is 4), v is 2, 3, 4, 5, or 6 (e.g., v is 3), and $R^{10A}$, $R^{10B}$, $R^{11A}$, and $R^{11B}$ are independently H, methyl, ethyl, propyl, butyl, allyl, butenyl, pentenyl, phenyl, or benzyl (e.g., H and/or methyl).

In yet another aspect, in formula (V), M is Ti, Zr, or Hf; Cp is a cyclopentadienyl or a fluorenyl group; m is 2; n is 1 or 2; each $R^A$ independently is H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, or tolyl; and E is a substituted or unsubstituted bridging chain of 3 to 6 carbon atoms or 2 to 6 silicon atoms. In a further aspect, E can be a bridging chain having the formula $-(CR^{10A}R^{10B})_u-$ or the formula $-(SiR^{11A}R^{11B})_v-$, where u is 3, 4, 5, or 6 (e.g., u is 4), v is 2, 3, 4, 5, or 6 (e.g., v is 3), and $R^{10A}$, $R^{10B}$, $R^{11A}$, and $R^{11B}$ are independently H, methyl, ethyl, propyl, butyl, allyl, butenyl, pentenyl, phenyl, or benzyl (e.g., H and/or methyl).

Optionally, methods disclosed herein to produce a stereo-enriched ansa-metallocene compound having formula (I) or a stereo-enriched ansa-metallocene compound having formula (V) can further comprise a step of isolating and/or purifying the rac isomer of the compound of formula (I) or formula (V). For example, a recrystallization step from a solvent, or from a mixture of solvents, can be employed. Suitable solvents can include the ether, aliphatic hydrocarbon, and aromatic hydrocarbon solvents selections disclosed above, as well as chlorinated hydrocarbons, and combinations thereof. For example, representative solvent mixtures can comprise two or more of the following solvents: toluene, pentane, hexane, heptane, $CH_2Cl_2$, diethyl ether, THF, and the like. Other purification and/or isolation techniques can be used in the practice of this invention, and these include, but are not limited to, distillation, chromatography, crystallization, extraction, evaporation, sublimation, washing, decanting, filtering, drying, and the like, including combinations thereof.

Rac-Ansa-Metallocene Compounds and Compositions

The present invention also is directed to racemic ansa-metallocene compounds and compositions that are stereo-enriched in rac isomers. In accordance with an aspect of this invention, Applicants contemplate a rac-ansa-metallocene compound having the formula:

and a rac-ansa-metallocene compound having the formula (V):

Additionally, Applicants contemplate compositions comprising an ansa-metallocene compound having formula (I) or formula (V) with a rac:meso isomer ratio of greater than 4:1, or greater than about 5:1, or greater than about 10:1, or greater than about 15:1. For instance, the rac:meso isomer ratio can fall within a range from 4:1 to about 100:1, such as, for example, from about 5:1 to about 90:1, from about 6:1 to about 75:1, from about 8:1 to about 50:1, or from about 10:1 to about 40:1. In another aspect, the amount of the meso isomer can be less than 25% of the amount of the rac isomer, or less than about 20%, or less than about 15%, or less than about 10%, or less than about 5%.

As would be recognized by those of skill in the art, formulas (I) and (V) apply only to compounds that exhibit chirality, i.e., compounds having prochiral Cp groups. In formulas (I) and (V), M, Cp, E, R, $R^A$, m, and n can be any of the selections described above in relation to the method of synthesizing a stereo-enriched ansa-metallocene from the compound having formula (II) and the unchelated amine compound having formula (III).

In accordance with one aspect of this invention, M in formulas (I) and (V) can be Ti, Zr, Hf, Cr, Sc, Y, La, or a lanthanide; or alternatively, M can be Ti, Zr, or Hf. E can be a substituted or unsubstituted bridging chain of 3 to 6 carbon atoms or 2 to 6 silicon, germanium, or tin atoms (e.g., 2 silicon atoms); or alternatively, E can be a bridging chain having the formula —$(CR^{10A}R^{10B})_u$— or the formula —$(SiR^{11A}R^{11B})_v$—, wherein u is 3, 4, or 5; v is 2, 3, or 4, and $R^{10A}$, $R^{10B}$, $R^{11A}$, and $R^{11B}$ are independently H, methyl, ethyl, propyl, butyl, allyl, butenyl, pentenyl, phenyl, or benzyl. Each R in formula (I) independently can be H, a hydrocarbyl, hydrocarbylsilyl, hydrocarbylamino, or hydrocarbyloxide group having up to 12 carbon atoms, or each $NR_2$ group can be a heterocyclic group having up to 12 carbon atoms; or alternatively, each R independently can be H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, benzyl, or trimethylsilyl. Each $R^A$ independently can be H or a hydrocarbyl, hydrocarbylsilyl, hydrocarbylamino, or hydrocarbyloxide group having up to 12 carbon atoms; or alternatively, each $R^A$ independently can be H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, tolyl, or benzyl.

In accordance with another aspect of this invention, in formulas (I) and (V), M is Ti, Zr, or Hf; Cp is an indenyl group; m is 2; n is 0; and each R in formula (I) independently is methyl, ethyl, propyl, butyl, pentyl, hexyl, heptyl, octyl, nonyl, decyl, or trimethylsilyl. In these and other aspects, E can be a substituted or unsubstituted bridging chain of 3 to 6 carbon atoms or 2 to 6 silicon atoms. In a further aspect, E can be a bridging chain having the formula —$(CR^{10A}R^{10B})_u$— or the formula —$(SiR^{11A}R^{11B})_v$—, where u is 3, 4, 5, or 6 (e.g., u is 4), v is 2, 3, 4, 5, or 6 (e.g., v is 3), and $R^{10A}$, $R^{10B}$, $R^{11A}$, and $R^{11B}$ are independently H, methyl, ethyl, propyl, butyl, allyl, butenyl, pentenyl, phenyl, or benzyl (e.g., H and/or methyl).

Yet, in accordance with another aspect of this invention, in formulas (I) and (V), M is Ti, Zr, or Hf; Cp is a cyclopentadienyl or a fluorenyl group; m is 2; n is 1 or 2; each $R^A$ independently is H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, or tolyl; and each R in formula (I) independently is methyl, ethyl, propyl, butyl, pentyl, hexyl, heptyl, octyl, nonyl, decyl, or trimethylsilyl. In these and other aspects, E can be a substituted or unsubstituted bridging chain of 3 to 6 carbon atoms or 2 to 6 silicon atoms. In a further aspect, E can be a bridging chain having the formula —$(CR^{10A}R^{10B})_u$— or the formula —$(SiR^{11A}R^{11B})_v$—, where u is 3, 4, 5, or 6 (e.g., u is 4), v is 2, 3, 4, 5, or 6 (e.g., v is 3), and $R^{10A}$, $R^{10B}$, $R^{11A}$, and $R^{11B}$ are independently H, methyl, ethyl, propyl, butyl, allyl, butenyl, pentenyl, phenyl, or benzyl (e.g., H and/or methyl).

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Unless otherwise noted, all operations were performed under purified nitrogen or vacuum using standard Schlenk of glovebox techniques. $Et_2O$ and THF were purchased anhydrous from Aldrich and used as received. Toluene (Fisher Scientific) was degassed and stored over activated 13× molecular sieves under nitrogen. $Me_4Si_2Cl_2$, indene (technical grade), $ZrCl_4$ and n-BuLi solution (2.5 M in hexanes) were purchased from Sigma-Aldrich and used as received.

Nuclear Magnetic Resonance (NMR) spectra were obtained on a Varian Mercury Plus 300 NMR spectrometer. $CDCl_3$ and $C_6D_6$ were purchased from Cambridge Isotope Laboratories, degassed and stored over activated 13× molecular sieves under nitrogen. NMR spectra were recorded using capped or J. Young NMR tubes at ambient probe conditions. $^1H$ chemical shifts are reported versus $SiMe_4$ and were determined by reference to the residual $^1H$ and solvent peaks. Coupling constants are reported in Hz.

Example 1

Synthesis of an Unchelated Amine Compound

In Example 1, the unchelated amine compound $Zr(NEt_2)_2Cl_2(THF)_2$ having the following structure was synthesized:

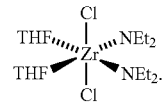

The unchelated amine compound was synthesized by following the procedure described in Brenner et al., Z. Anorg. Allg. Chem., 1995, 621, 2021-2024, the disclosure of which is incorporated herein by reference in its entirety.

Example 2

Synthesis of a Rac/Meso Bridged Ligand (L1)

A bridged ligand compound (abbreviated L1) with the following structure was synthesized in Example 2:

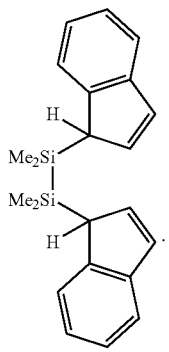

The bridged ligand compound rac/meso-L1 was synthesized by a modified procedure based on the method described in the Journal of Organometallic Chemistry, 1999, 585, 18-25, the disclosure of which is incorporated herein by reference in its entirety. A solution of indene (95 mole percent purity, 10 mL, 81.8 mmol) in $Et_2O$ (200 mL) was prepared, cooled in dry ice/acetone, and charged with a solution of n-BuLi (33 mL, 2.5 M in hexanes, 83 mmol) by syringe over 1 min. The solution was stirred and allowed to warm slowly to approximately 22° C. over 16 hr. A separate solution of 1,2-dichloro-1,1,2,2-tetramethyldisilane (7.54 g, 40.3 mmol) in $Et_2O$ (100 mL) was prepared and cooled in ice water. The prepared Li-Ind solution was added dropwise by cannula to the disilane solution over 1 hr. The resulting pale-yellow suspension was stirred and warmed slowly to approximately 22° C. over 16 hr. The solution was evaporated under vacuum resulting in a beige solid. Toluene (75 mL) was added by cannula and the resulting suspension was centrifuged. The supernatant solution was removed by cannula, and this toluene extraction procedure was repeated to produce two toluene extracts. The two extracts were combined and evaporated to a volume of approximately 75 mL. The resulting suspension was warmed to 40° C. in a hot water bath, and stirred to dissolve the precipitated solid. The stirring was halted upon complete dissolution of the solid, and then the solution was allowed to cool slowly to approximately 22° C. for about 16 hours. The supernatant solution was decanted by cannula and the resulting precipitate was dried under vacuum to obtain rac/meso-L1 as an amber, crystalline solid (5.55 g). The supernatant solution was concentrated and a recrystallization procedure analogous to the aforementioned was repeated twice to obtain two additional amounts of rac/meso-L1 (2.83 g and 1.52 g, respectively) exhibiting comparable NMR purity to that of the first. Total isolated yield of rac/meso-L1 was 9.90 g, 71%. $^1$H NMR data indicated the presence of a 2/1 mixture of diastereomers, neither of which could be unambiguously characterized as rac or meso due to the presence of symmetry elements in both cases. Key $^1$H NMR data for the major isomer ($CDCl_3$): δ 6.28 (dd, J=5, 2; 2H, $C_5$-Ind), 3.16 (s, 2H, $C_5$-Ind), −0.18 (s, 6H, $SiMe_2$), −0.30 (s, 6H, $SiMe_2$). Key $^1$H NMR data for the minor isomer ($CDCl_3$): δ 6.42 (dd, J=5, 2; 2H, $C_5$-Ind), 3.27 (s, 2H, $C_5$-Ind), −0.10 (s, 6H, $SiMe_2$), −0.45 (s, 6H, $SiMe_2$).

Comparative Example 3

Synthesis of a Rac/Meso Bridged Bis-Indenyl Metallocene Compound (MET1)

A rac/meso bridged bis-indenyl metallocene compound (abbreviated MET1) with the following structure was synthesized in Comparative Example 3:

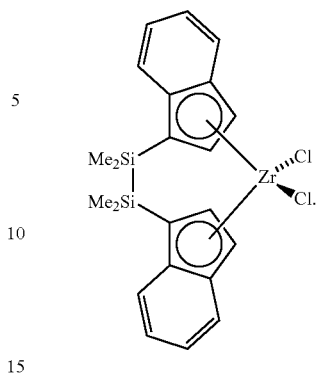

A solution of rac/meso-L1 (2.82 g, 8.14 mmol) from Example 2 in $Et_2O$ (75 mL) was prepared, cooled to −5° C., and charged with a solution of n-BuLi (6.7 mL, 2.5 M in hexanes, 17 mmol) by syringe over 30 sec. The mixture was stirred for 10 min, and then allowed to warm to approximately 22° C. over 16 hr while stirring. A suspension of $ZrCl_4$ (1.90 g, 8.14 mmol) in toluene (50 mL) was prepared and cooled to −5° C. The lithiated bis(indenide) solution obtained from rac/meso-L1 was added to the stirred zirconium suspension by cannula over 30 sec. The cooling bath was removed and the resulting yellow-orange suspension was stirred and warmed to approximately 22° C. over 16 hr. The yellow suspension was evaporated under vacuum and toluene (50 mL) was added by cannula. The suspension was centrifuged, and the supernatant solution was removed by cannula and evaporated under vacuum at 40° C. to obtain rac/meso-MET1 (1:1 rac/meso) as a yellow solid. The solid was recrystallized twice from toluene to obtain pure meso-MET1. NMR data for these samples in $CDCl_3$ solution matched those reported in the Journal of Organometallic Chemistry, 1999, 585, 18-25, for the MET1 compound.

Example 4

Synthesis of a Rac Bridged Bis-Indenyl Metallocene Compound (MET 2)

A rac bridged bis-indenyl metallocene compound (abbreviated MET2) with the following structure was synthesized in Example 4:

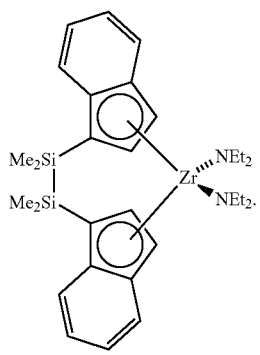

A solution of rac/meso-L1 (1.988 g, 5.735 mmol) from Example 2 in $Et_2O$ (100 mL) was prepared, cooled to −5° C., and charged with a solution of n-BuLi (4.6 mL, 2.5 M in hexanes, 11.5 mmol) by syringe over 10 sec. The mixture was warmed to approximately 22° C. over 2.5 hr to obtain a white suspension. THF (1 mL) was added by syringe to obtain an amber solution. A suspension of the unchelated amine compound of Example 1, Zr(NEt$_2$)$_2$Cl$_2$(THF)$_2$ (2.584 g, 5.735 mmol), in Et$_2$O (50 mL) was prepared and cooled to −5° C. The lithium solution obtained from rac/meso-L1 was added by cannula to the stirred zirconium suspension over 2 min. The resulting yellow suspension was stirred in the cooling bath for 1.5 hr and then warmed to approximately 22° C. over 16 hr. The mixture was evaporated under vacuum, charged with toluene (25 mL), and centrifuged. The resulting clear, red supernatant was decanted by cannula, evaporated under vacuum, and dried under vacuum to obtain rac-MET2 as a viscous, red oil that slowly crystallized to a red wax over several days (quantitative yield, >90% NMR purity). $^1$H NMR (C$_6$D$_6$): δ 7.85 (m, 2H, C$_6$-Ind), 7.48 (m, 2H, C$_6$-Ind), 6.97 (m, 4H, C$_6$-Ind), 6.58 (d, J=3, 2H, C$_5$-Ind), 6.20 (dd, J=3, 1; 2H, C$_5$-Ind), 3.16 (m, 4H, NCH$_2$), 3.03 (m, 4H, NCH$_2$), 0.83 (t, J=8, 12H, NCH$_2$CH$_3$), 0.71 (s, 6H, SiMe), 0.53 (s, 6H, SiMe). The $^1$H-NMR spectra for the final product of Example 4 is illustrated in FIG. 1.

Example 5

Synthesis of a Rac Bridged Bis-Indenyl Metallocene Compound (MET2)

A rac bridged bis-indenyl metallocene compound (abbreviated MET2) with the following structure was synthesized in Example 5:

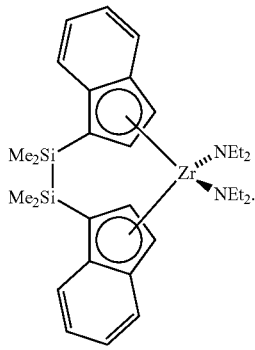

A solution of rac/meso-L1 (1.02 g, 2.94 mmol) from Example 2 in THF (25 mL) was prepared, cooled in dry ice/acetone, and charged with a solution of n-BuLi (2.4 mL, 2.5 M in hexanes, 5.9 mmol) by syringe over 5 sec. The mixture was warmed to approximately 22° C. over 16 hr. A solution of the unchelated amine compound of Example 1, Zr(NEt$_2$)$_2$Cl$_2$(THF)$_2$ (1.33 g, 2.94 mmol) in THF (25 mL) was prepared, and the lithium solution obtained from rac/meso-L1 was added by cannula over 1 min at approximately 22° C. The resulting mixture was stirred for 1 hr, evaporated under vacuum, dried under vacuum, charged with toluene (50 mL), and centrifuged. The resulting clear supernatant solution was decanted by cannula, and evaporated under vacuum to obtain rac-MET2 (quantitative yield, >90% NMR purity). $^1$H NMR data for the final product of Example 5 matched that obtained in Example 4.

Constructive Example 6

Constructive Synthesis of Rac-MET1 from Rac-MET2

A rac bridged bis-indenyl metallocene compound (abbreviated MET2) with the following structure:

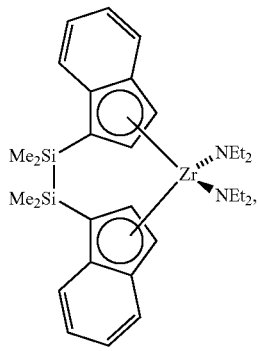

as prepared in Example 4 or 5, can be converted to a rac bridged bis-indenyl metallocene compound (abbreviated MET1) with the following structure:

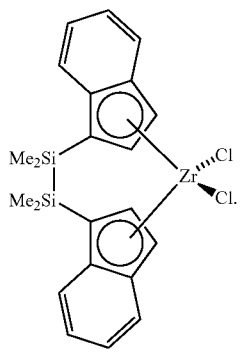

Hence, rac-MET1 can be synthesized from rac-MET2. The procedure described in U.S. Pat. No. 6,207,608, the disclosure of which is incorporated herein by reference in its entirety, can be used to produce the dichloride metallocene, rac-MET1.

Under nitrogen atmosphere, a solution of Me$_2$NH.HCl (1 mmol) in CH$_2$Cl$_2$ (20 mL) can be added dropwise to a solution of rac-MET2 (0.5 mmol) at −78° C. while stirring. The resulting solution can be stirred approximately 22° C. for 30 min. The solvent can be removed under reduced pressure, and the resulting solid can be washed with hexane (15 mL), then extracted with toluene (70 mL). Removal of the solvent from the toluene extract under reduced pressure can result in rac-MET1 with greater than 90% rac stereoselectivity or stereospecificity, and at an overall product yield of over 80% or, alternatively, over 90%.

We claim:

1. A racemic ansa-metallocene compound having formula (I):

E(CpR$^A_n$)$_2$M(NR$_2$)$_m$           (I);

wherein:
  M is Ti, Zr, Hf, Cr, Sc, Y, La, or a lanthanide;
  Cp is a cyclopentadienyl, indenyl, or fluorenyl group;
  E is a substituted or unsubstituted bridging chain of 2 to 8 silicon, germanium, or tin atoms, wherein any substituents on atoms of the bridging chain independently are H or a hydrocarbyl group having up to 18 carbon atoms;
  each R independently is H, a hydrocarbyl, hydrocarbylsilyl, hydrocarbylamino, or hydrocarbyloxide group having up to 18 carbon atoms, or each NR$_2$ group is a heterocyclic group having up to 18 carbon atoms;

each R$^A$ independently is H or a hydrocarbyl, hydrocarbylsilyl, hydrocarbylamino, or hydrocarbyloxide group having up to 18 carbon atoms;

m is 2 when M is Ti, Zr, or Hf;

m is 1 when M is Cr, Sc, Y, La, or a lanthanide;

n is 0, 1, 2, 3, or 4 when Cp is an indenyl group; and n is 1, 2, 3, or 4 when Cp is a cyclopentadienyl or a fluorenyl group.

2. The compound of claim 1, wherein:

M is Ti, Zr, or Hf;

Cp is an indenyl group;

n is 0; and

E is a substituted or unsubstituted bridging chain of 2 to 6 silicon, germanium, or tin atoms.

3. The compound of claim 2, wherein E is a substituted or unsubstituted bridging chain of 2 silicon, germanium, or tin atoms.

4. The compound of claim 1, wherein:

M is Ti, Zr, or Hf;

Cp is an indenyl group;

n is 0;

E is a bridging chain having the formula —(SiR$^{11A}$R$^{11B}$)$_2$—, wherein R$^{11A}$ and R$^{11B}$ are independently H, methyl, ethyl, propyl, butyl, allyl, butenyl, pentenyl, phenyl, or benzyl; and each R independently is H or a hydrocarbyl group having up to 18 carbon atoms, or each NR$_2$ group is a heterocyclic group having up to 18 carbon atoms.

5. The compound of claim 4, wherein E is —SiMe$_2$-SiMe$_2$-.

6. The compound of claim 1, wherein:

M is Ti, Zr, or Hf;

Cp is an indenyl group;

n is 1 or 2; and

E is a substituted or unsubstituted bridging chain of 2 silicon, germanium, or tin atoms.

7. The compound of claim 6, wherein:

each R independently is H or a hydrocarbyl group having up to 18 carbon atoms, or each NR$_2$ group is a heterocyclic group having up to 18 carbon atoms; and each R$^A$ independently is H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, tolyl, or trimethylsilyl.

8. The compound of claim 7, wherein E is a bridging chain having the formula —(SiR$^{11A}$R$^{11B}$)$_2$—, wherein R$^{11A}$ and R$^{11B}$ are independently H or a hydrocarbyl group having up to 18 carbon atoms.

9. The compound of claim 7, wherein E is —SiMe$_2$-SiMe$_2$-.

10. A stereo-enriched ansa-metallocene compound having formula (I) and a molar ratio of rac isomer to meso isomer of greater than 4:1:

E(CpR$^A_n$)$_2$M(NR$_2$)$_m$    (I);

wherein:

M is Ti, Zr, Hf, Cr, Sc, Y, La, or a lanthanide;

Cp is a cyclopentadienyl, indenyl, or fluorenyl group;

E is a substituted or unsubstituted bridging chain of 3 to 8 carbon atoms or 2 to 8 silicon, germanium, or tin atoms, wherein any substituents on atoms of the bridging chain independently are H or a hydrocarbyl group having up to 18 carbon atoms;

each R independently is H, a hydrocarbyl, hydrocarbylsilyl, hydrocarbylamino, or hydrocarbyloxide group having up to 18 carbon atoms, or each NR$_2$ group is a heterocyclic group having up to 18 carbon atoms;

each R$^A$ independently is H or a hydrocarbyl, hydrocarbylsilyl, hydrocarbylamino, or hydrocarbyloxide group having up to 18 carbon atoms;

m is 2 when M is Ti, Zr, or Hf;

m is 1 when M is Cr, Sc, Y, La, or a lanthanide;

n is 0, 1, 2, 3, or 4 when Cp is an indenyl group; and n is 1, 2, 3, or 4 when Cp is a cyclopentadienyl or a fluorenyl group.

11. The compound of claim 10, wherein:

the molar ratio of rac isomer to meso isomer is in a range from about 6:1 to about 100:1;

M is Ti, Zr, or Hf;

Cp is an indenyl group;

n is 0;

E is a substituted or unsubstituted bridging chain of 3 to 6 carbon atoms or 2 to 6 silicon, germanium, or tin atoms; and each R independently is methyl, ethyl, propyl, butyl, pentyl, hexyl, heptyl, octyl, nonyl, decyl, or trimethylsilyl.

12. The compound of claim 11, wherein E is a substituted or unsubstituted bridging chain of 2 silicon, germanium, or tin atoms.

13. The compound of claim 10, wherein:

the molar ratio of rac isomer to meso isomer is in a range from about 5:1 to about 100:1; and the stereo-enriched ansa-metallocene compound having formula (I) is:

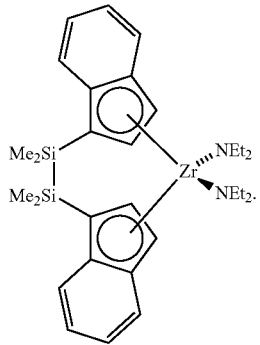

14. The compound of claim 10, wherein:

the molar ratio of rac isomer to meso isomer is in a range from about 6:1 to about 100:1;

M is Ti, Zr, or Hf;

n is 1 or 2;

E is a substituted or unsubstituted bridging chain of 3 to 6 carbon atoms or 2 to 6 silicon, germanium, or tin atoms;

each R independently is methyl, ethyl, propyl, butyl, pentyl, hexyl, heptyl, octyl, nonyl, decyl, or trimethylsilyl; and each R$^A$ independently is H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, tolyl, or trimethylsilyl.

15. The compound of claim 14, wherein:

Cp is an indenyl group; and

E is a substituted or unsubstituted bridging chain of 2 silicon, germanium, or tin atoms.

16. A stereo-enriched ansa-metallocene compound having formula (V) and a molar ratio of rac isomer to meso isomer of greater than or equal to 6:1:

$$E(CpR^A{}_n)_2M(Cl)_m \quad (V);$$

wherein:
M is Ti, Zr, Hf, Cr, Sc, Y, La, or a lanthanide;
Cp is a cyclopentadienyl, indenyl, or fluorenyl group;
E is a substituted or unsubstituted bridging chain of 3 to 8 carbon atoms or 2 to 8 silicon, germanium, or tin atoms, wherein any substituents on atoms of the bridging chain independently are H or a hydrocarbyl group having up to 18 carbon atoms;
each $R^A$ independently is H or a hydrocarbyl, hydrocarbylsilyl, hydrocarbylamino, or hydrocarbyloxide group having up to 18 carbon atoms;
m is 2 when M is Ti, Zr, or Hf;
m is 1 when M is Cr, Sc, Y, La, or a lanthanide;
n is 0, 1, 2, 3, or 4 when Cp is an indenyl group; and
n is 1, 2, 3, or 4 when Cp is a cyclopentadienyl or a fluorenyl group.

17. The compound of claim 16, wherein:
the molar ratio of rac isomer to meso isomer is in a range from 6:1 to about 100:1;
M is Ti, Zr, or Hf;
Cp is an indenyl group;
n is 0;
E is a substituted or unsubstituted bridging chain of 3 to 6 carbon atoms or 2 to 6 silicon, germanium, or tin atoms.

18. The compound of claim 17, wherein E is a substituted or unsubstituted bridging chain of 2 silicon, germanium, or tin atoms.

19. The compound of claim 17, wherein E is —SiMe$_2$-SiMe$_2$-.

20. The compound of claim 16, wherein:
the molar ratio of rac isomer to meso isomer is in a range from 6:1 to about 100:1;
M is Ti, Zr, or Hf;
n is 1 or 2;
E is a substituted or unsubstituted bridging chain of 3 to 6 carbon atoms or 2 to 6 silicon, germanium, or tin atoms; and
each $R^A$ independently is H, methyl, ethyl, propyl, butyl, pentyl, hexyl, heptyl, octyl, nonyl, decyl, ethenyl, propenyl, butenyl, pentenyl, hexenyl, heptenyl, octenyl, nonenyl, decenyl, phenyl, benzyl, tolyl, or trimethylsilyl.

21. The compound of claim 20, wherein:
Cp is an indenyl group; and
E is a substituted or unsubstituted bridging chain of 2 silicon, germanium, or tin atoms.

22. The compound of claim 20, wherein E is —SiMe$_2$-SiMe$_2$-.

* * * * *